United States Patent
Mizushima et al.

(10) Patent No.: US 12,101,869 B2
(45) Date of Patent: Sep. 24, 2024

(54) PARTICLE ACCELERATOR AND PARTICLE BEAM THERAPY APPARATUS

(71) Applicant: National Institutes for Quantum Science and Technology, Chiba (JP)

(72) Inventors: Kota Mizushima, Chiba (JP); Toshiyuki Shirai, Chiba (JP)

(73) Assignee: National Institutes for Quantum Science and Technology, Chiba (JP)

( * ) Notice: Subject to any disclaimer, the term of this patent is extended or adjusted under 35 U.S.C. 154(b) by 173 days.

(21) Appl. No.: 17/999,995

(22) PCT Filed: Jan. 29, 2021

(86) PCT No.: PCT/JP2021/003180
§ 371 (c)(1),
(2) Date: Nov. 28, 2022

(87) PCT Pub. No.: WO2021/260988
PCT Pub. Date: Dec. 30, 2021

(65) Prior Publication Data
US 2023/0209696 A1    Jun. 29, 2023

(30) Foreign Application Priority Data

Jun. 23, 2020 (JP) .................. 2020-108088

(51) Int. Cl.
*H05H 7/04* (2006.01)
*A61N 5/10* (2006.01)
(Continued)

(52) U.S. Cl.
CPC ............ *H05H 7/04* (2013.01); *A61N 5/1078* (2013.01); *H05H 7/001* (2013.01); *H05H 13/04* (2013.01);
(Continued)

(58) Field of Classification Search
CPC .......... H05H 7/04; H05H 7/001; H05H 13/04; H05H 2007/046; H05H 2277/11; A61N 5/1078; A61N 5/1077; A61N 2005/1087
See application file for complete search history.

(56) References Cited

U.S. PATENT DOCUMENTS

| | | | | |
|---|---|---|---|---|
| 2012/0267543 | A1* | 10/2012 | Noda | A61N 5/10 |
| | | | | 315/503 |
| 2013/0193353 | A1* | 8/2013 | Ikeda | H05H 13/04 |
| | | | | 315/503 |
| 2021/0387022 | A1* | 12/2021 | Raymond | G21K 1/10 |

FOREIGN PATENT DOCUMENTS

| | | | |
|---|---|---|---|
| JP | 2012-022776 | * | 2/2012 |
| JP | 2012022776 A | | 2/2012 |

(Continued)

OTHER PUBLICATIONS

Machine Translation of JP2012-022776 (Year: 2012).*
PCT Office, International Search Report issued in PCT/JP2021/003180 dated Apr. 6, 2021.

Primary Examiner — Alexander H Taningco
Assistant Examiner — Pedro C Fernandez
(74) Attorney, Agent, or Firm — Wood Herron & Evans LLP

(57) ABSTRACT

Disclosed a particle accelerator that accelerates a charged particle beam while circulating the charged particle beam as a circulating beam and outputs some of the circulating beam as an output beam, the particle accelerator including: a first deflection section and a second deflection sections each having a deflection electromagnet; a first straight section, a second straight section, and third straight section each not having the deflection electromagnet; and a control unit, wherein a preceding output deflector of the first straight section deflects some of the circulating beam toward an inner side of a circulating trajectory of the circulating beam
(Continued)

to separate the some of the circulating beam as an output beam, wherein a succeeding output deflector of the third straight section deflects the output beam separated from the circulating beam by the preceding output deflector toward an outer side of the circulating trajectory of the circulating beam, and wherein the control unit controls at least the quadrupole electromagnet such that a phase advance of a betatron oscillation of the output beam is 270±45 degrees in a section from the preceding output deflector to the succeeding output deflector.

13 Claims, 14 Drawing Sheets

(51) Int. Cl.
*H05H 7/00* (2006.01)
*H05H 13/04* (2006.01)

(52) U.S. Cl.
CPC ............... *A61N 2005/1087* (2013.01); *H05H 2007/046* (2013.01); *H05H 2277/11* (2013.01)

(56) References Cited

FOREIGN PATENT DOCUMENTS

| | | | |
|---|---|---|---|
| JP | 2012234805 | A | 11/2012 |
| JP | 2014053194 | A | 3/2014 |
| JP | 2016081729 | A | 5/2016 |

* cited by examiner

FIG. 11
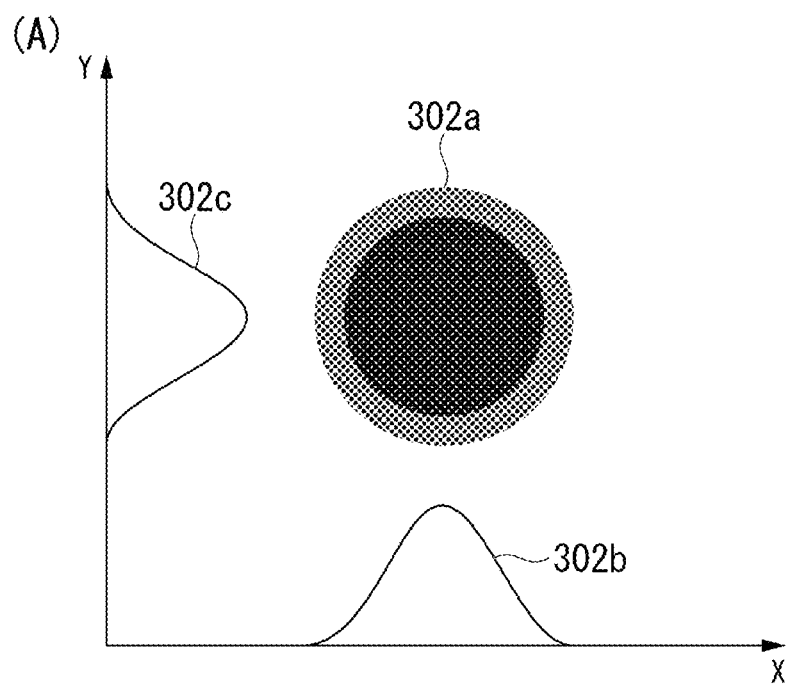
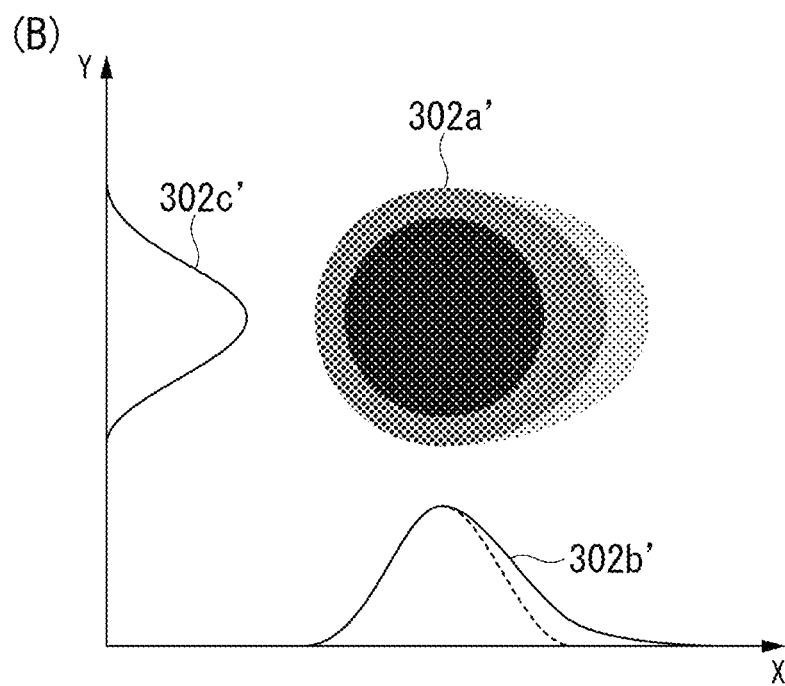

PARTICLE ACCELERATOR AND PARTICLE BEAM THERAPY APPARATUS

TECHNICAL FIELD

The present invention relates to a particle accelerator and a particle beam therapy apparatus.

Priority is claimed on Japanese Patent Application No. 2020-108088, filed Jun. 23, 2020, the content of which is incorporated herein by reference.

BACKGROUND ART

Particle accelerators are widely used in various fields such as science, industry, and medicine as apparatuses for generating high-energy charged particles. In the field of particle beam therapy, circular accelerators are currently used because they can accelerate charged particles to have high energy in a limited space. In addition, in order to reduce the introduction cost of particle beam therapy facilities, the number of cases of reducing a size of a particle beam therapy apparatus using superconducting technology is increasing. If a superconductive electromagnet with a high magnetic field is used, even high-energy charged particles can be deflected with a short radius of curvature, and thus it is possible to reduce a size of the circular accelerator. A circular accelerator occupies a large installation area in a particle beam therapy apparatus, and it is very effective to use a superconductive electromagnet in the circular accelerator to reduce the size of the particle beam therapy apparatus.

In a synchrotron which is one of the circular accelerators, while a charged particle beam is deflected and circulated with a magnetic field generated by an electromagnet, acceleration energy is given to the charged particle beam in a high frequency acceleration cavity, and the magnetic field generated by the electromagnet is increased in accordance with a change in energy of the charged particle beam. Therefore, it is possible to accelerate the charged particle beam with various types of energy while maintaining a stable circulating trajectory of the charged particle beam, and it is possible to extract (output) the charged particle beam to the outside from the synchrotron by an output deflector. The charged particle beam circulating in the synchrotron passes through the same trajectory even if its energy changes as it is accelerated. Therefore, each configuration device such as an electromagnet is relatively small and efficient and suitable for generating high-energy charged particles.

In the related art, a synchrotron having a substantially square shape as a whole, which is constituted by a short straight section and a curved section having a large curvature in order to reduce a size of the synchrotron, has been proposed. In such a synchrotron, since each straight section is short, the straight section on an upstream side of the curved section is provided with a preceding output deflector for separating an output beam from a circulating beam, and the straight section on a downstream side of the curved section is provided with a succeeding output deflector for extracting the output beam separated from the circulating beam to the outside. On the other hand, the curved section having a large curvature is provided with a deflection electromagnet such as a superconductive electromagnet which requires a cooling means.

FIG. 9 is a diagram showing such a particle accelerator of the related art and a particle beam therapy apparatus to which such a particle accelerator of the related art is applied. FIG. 10 is a diagram showing a relationship between a passage region (a hatched portion in FIG. 10) of a circulating beam 131 and a trajectory of an output beam 132 in an example of the related art shown in FIG. 9. In FIG. 10, an S-axis direction indicates a traveling direction of the circulating beam 131. An X axis included in a plane orthogonal to the S axis corresponds to a deflection direction of a deflection electromagnet 102. A Y axis included in the plane orthogonal to the S axis is orthogonal to the X axis.

In reducing a size of a synchrotron (a particle accelerator) 100, extracting (outputting) an accelerated high-energy beam without loss is a major problem. In order to effectively reduce the size, it is necessary not only to increase a magnetic field of the deflection electromagnet 102 and shorten a deflection section 121, but also to shorten straight sections 111 and 112 together. However, in order to extract the output beam 132 to the outside from the synchrotron (the particle accelerator) 100 without loss, it is necessary to separate the output beam 132 and the circulating beam 131 from each other with a preceding output deflector 108 and to largely bend the output beam 132 to the outside from the synchrotron (the particle accelerator) 100 with a succeeding output deflector 109. However, in order to do this, a long space for arranging each of the preceding-stage output deflector 108 and the succeeding-stage output deflector 109 is required, which conflicts with shortening the straight sections 111 and 112.

Therefore, in the synchrotron (the particle accelerator) 100 of the related art shown in FIG. 9 aimed at reduction in size, a configuration in which the preceding output deflector 108 and the succeeding output deflector 109 are divisibly disposed in two straight sections (a first straight section 111 and a second straight section 112) has been adopted. Specifically, the preceding output deflector 108 is disposed in the first straight section 111, a first deflection section 121 is connected to a downstream side of the first straight section 111, and the first deflection section 121 is constituted by one deflection electromagnet 102 or a combination of two or more deflection electromagnets 102 and a short straight section. In addition, the succeeding output deflector 109 is disposed in the second straight section 112 on a downstream side of the first deflection section 121.

However, in this method, as shown in FIG. 10, in order to avoid beam loss, the circulating beam 131 and the output beam 132 have to be largely separated from each other at a position of the succeeding output deflector 109. Therefore, the output beam 132 needs to be largely deflected by the preceding output deflector 108, and in such a case, the trajectory of the output beam 132 in the first deflection section 121 deviates largely from the passage region (the hatched portion in FIG. 10) of the circulating beam 131. The deflection electromagnet 102 of the first deflection section 121 also has to transport the output beam 132 far from this central trajectory, and thus, inevitably, a magnetic field generation region of the deflection electromagnets 102 of the first deflection section 121 is greatly widened. As a result, the size and cost of the deflection electromagnet 102 of the first deflection section 121 are inevitably increased. In particular, in a case where a superconductive electromagnet is used as the deflection electromagnet 102 of the first deflection section 121, the widening of the magnetic field generation region has been a major problem because it increases the manufacturing difficulty or cost and the operating cost including cooling.

Specifically, in this method, the deflection electromagnet 102 of the first deflection section 121 having a curved shape has to deflect the output beam 132 that largely deviates from the circulating beam 131 along the curved shape of the first deflection section 121. Therefore, the magnetic field generation region of the deflection electromagnet 102 such as a superconductive electromagnet provided in the first deflection section 121 needs to be greatly widened, which increases the cost and increases the size.

In particular, in the small synchrotron (the particle accelerator) 100 as shown in FIG. 9, in order to increase space efficiency by reducing the number of components, it is important to reduce the number of pairs of straight sections such as the first straight section 111 and the second straight section 112 and deflection sections such as the first deflection section 121, and it is desirable that the number of pairs of straight sections and deflection sections be 6 or less and ideally 4 or less. In such a case, a deflection angle of a charged particle beam per deflection section also increases, and a convergence action of the charged particle beam caused by the deflection electromagnet 102 is strengthened. Therefore, the preceding output deflector 108 needs to more largely deviate the output beam 132 from the central trajectory (the hatched portion in FIG. 10) of the circulating beam 131. As a result, the magnetic field generation region of the deflection electromagnet 102 is further widened.

Further, another problem caused by the output beam 132 passing through a trajectory largely deviating from the central trajectory of the circulating beam 131 is that the output beam 132 is greatly affected by a nonlinear magnetic field component generated by the deflection electromagnet 102 and a particle distribution shape of the output beam 132 is distorted. Since it is very difficult to maintain the uniformity of the generated magnetic field over a wide range, generally, the further the distance from a center of the electromagnet is, the greater an error from an ideal magnetic field distribution is, and for this, the nonlinear magnetic field component is added. In a case where the charged particle beam passes through a position that is not very far from the center of the electromagnet, the influence of the nonlinear magnetic field component on the beam distribution is small. However, in a case where the charged particle beam passes through the trajectory far from the center of the electromagnet, the influence of the nonlinear magnetic field component on the charged particle beam is great, and a distribution shape of an irradiation beam 302 is distorted (see FIG. 11(B)).

FIG. 11 is a diagram for explaining an ideal two-dimensional cross-sectional distribution or the like of the irradiation beam 302. Specifically, FIG. 11(A) shows an example in which the charged particle beam passes through the center of the electromagnet and a shape of a two-dimensional cross-sectional distribution 302a of the irradiation beam 302 is not distorted. FIG. 11(B) shows an example in which the charged particle beam passes through the trajectory far from the center of the electromagnet and a shape of a two-dimensional cross-sectional distribution 302a' of the irradiation beam 302 is distorted. An X axis of each of FIGS. 11(A) and 11(B) corresponds to the X axis of FIG. 10, and a Y axis of each of FIGS. 11(A) and 11(B) corresponds to the Y axis of FIG. 10.

In the example in which the shape of the two-dimensional cross-sectional distribution 302a of the irradiation beam 302 shown in FIG. 11(A) is not distorted, the shape of the two-dimensional cross-sectional distribution 302a of the irradiation beam 302 is circular, and a shape of a horizontal projection profile 302b of the irradiation beam 302 is substantially the same as a shape of a vertical projection profile 302c.

In the example in which the shape of the two-dimensional cross-sectional distribution 302a' of the irradiation beam 302 shown in FIG. 11(B) is distorted, the shape of the two-dimensional cross-sectional distribution 302a' of the irradiation beam 302 is non-circular, and a shape of a horizontal projection profile 302b' of the irradiation beam 302 is different from a shape of a vertical projection profile 302c'.

As in the example shown in FIG. 11(B), in a case where the irradiation beam 302 having a two-dimensional cross-sectional distribution 302a' influenced by a strong nonlinear magnetic field component is used for particle beam therapy, a dose error increases, which may cause more damage in normal tissues.

In order to solve the above-described problems, the inventors of the present invention have proposed the method described in Patent Document 1.

In the technique described in Patent Document 1, a second output deflector denoted by reference sign 8c is provided immediately before a deflection electromagnet denoted by reference sign 6 in Patent Document 1, an output beam denoted by reference sign 11 separated from a circulating beam denoted by reference sign 10 by a first output deflector (a preceding output deflector) denoted by reference sign 8a is directed toward a central trajectory of the circulating beam by the second output deflector denoted by reference sign 8c. Therefore, the output beam obliquely traverses the central trajectory of the circulating beam in the deflection electromagnet denoted by reference sign 6, the output beam is bent again toward the central trajectory of the circulating beam by a converging electromagnet denoted by reference sign 7, and the output beam is extracted to the outside from a synchrotron by a final output deflector (a succeeding output deflector) denoted by reference sign 8b. As a result, in the technique described in Patent Document 1, in the deflection electromagnet denoted by reference sign 6, it is possible to reduce a size of a magnetic field generation region of the deflection electromagnet such as a superconductive electromagnet that requires a cooling means.

However, in the technique described in Patent Document 1, it is necessary to provide the second output deflector for directing the output beam toward the central trajectory of the circulating beam in a straight section on an upstream side of the deflection electromagnet denoted by reference sign 6. Therefore, the straight section on the upstream side of the deflection electromagnet denoted by reference sign 6 and a straight section opposite thereto are long, and the size of the entire synchrotron is increased.

Further, Patent Document 2 and Patent Document 3 describe a synchrotron and a particle beam therapy system using the synchrotron.

Specifically, paragraph 0007 of Patent Document 3 describes that it is designed such that a phase difference between a first output deflector and a second output deflector is close to 90 degrees. Further, paragraph 0010 of Patent Document 3 describes that it is necessary to make a phase advance between the first output deflector and the second output deflector close to 90 degrees+180 degrees×n. Furthermore, paragraph 0025 of Patent Document 3 describes that a phase difference between the first output deflector and a third output deflector is close to around 180°.

On the other hand, according to the techniques described in Patent Document 1 to Patent Document 3, it is not possible to reduce the size of the synchrotron by curbing the cost and the like while making the particle distribution shape of the output beam appropriate.

CITATION LIST

Patent Document

[Patent Document 1]
Japanese Unexamined Patent Application, First Publication No. 2016-081729
[Patent Document 2]
Japanese Unexamined Patent Application, First Publication No. 2012-234805
[Patent Document 3]
Japanese Unexamined Patent Application, First Publication No. 2012-022776

SUMMARY OF INVENTION

Technical Problem

In view of the above points, an object of the present invention is to provide a particle accelerator and a particle beam therapy apparatus that can achieve reduction in size.

Specifically, an object of the present invention is to provide a particle accelerator and a particle beam therapy apparatus that can reduce a magnetic field generation region required for a deflection electromagnet of a deflection section, reduce the overall cost associated with the deflection electromagnet, and achieve reduction in size of the particle accelerator.

Solution to Problem

According to an aspect of the present invention, there is provided a particle accelerator that accelerates a charged particle beam while circulating the charged particle beam as a circulating beam and outputs some of the circulating beam as an output beam, the particle accelerator including: a plurality of deflection sections each having a deflection electromagnet; a plurality of straight sections each not having the deflection electromagnet; and a control unit, wherein the plurality of straight sections include a first straight section having a preceding output deflector, a second straight section that is disposed on a downstream side of the first straight section in a traveling direction of the circulating beam and has a quadrupole electromagnet, and a third straight section that is disposed on a downstream side of the second straight section in the traveling direction of the circulating beam and has a succeeding output deflector, wherein the plurality of deflection sections include a first deflection section connecting the first straight section and the second straight section to each other, and a second deflection section connecting the second straight section and the third straight section to each other, wherein the preceding output deflector deflects some of the circulating beam toward one of an inner side and an outer side of a circulating trajectory of the circulating beam to separate the some of the circulating beam as an output beam, wherein the succeeding output deflector deflects the output beam separated from the circulating beam by the preceding output deflector toward the other of the inner side and the outer side of the circulating trajectory of the circulating beam, and wherein the control unit controls at least the quadrupole electromagnet such that a phase advance of a betatron oscillation of the output beam is 270±45 degrees in a section from the preceding output deflector to the succeeding output deflector.

In the particle accelerator according to the aspect of the present invention, the control unit may control at least the quadrupole electromagnet such that a phase advance of a betatron oscillation of the output beam is 270±45 degrees in a section from the preceding output deflector to the succeeding output deflector, and the control unit may control the preceding output deflector such that the output beam passes through the vicinity of a passage region of the circulating beam in the first deflection section, the output beam passes through a passage region of the circulating beam in the second deflection section or passes through the vicinity of the passage region of the circulating beam in the second deflection section, and the output beam passes through a position spaced apart from a passage region of the circulating beam in third straight section.

In the particle accelerator according to the aspect of the present invention, the first straight section and the third straight section may be disposed at positions facing each other on the circulating trajectory of the circulating beam.

In the particle accelerator according to the aspect of the present invention, the first straight section and the third straight section may extend parallel to each other.

In the particle accelerator according to the aspect of the present invention, each of the plurality of deflection sections may have the deflection electromagnet and a deflection section quadrupole electromagnet or have a quadrupole magnetic field generating mechanism for a deflection section obtained by integrating the deflection electromagnet and a quadrupole magnetic field coil, each of the plurality of straight sections may have the quadrupole electromagnet, and the control unit may adjust an amount of excitation of the deflection section quadrupole electromagnet of each of the plurality of deflection sections or an amount of excitation of the quadrupole magnetic field generating mechanism for a deflection section and an amount of excitation of the quadrupole electromagnet of each of the plurality of straight sections such that a phase advance of a betatron oscillation of the output beam is 270±45 degrees in a section from the preceding output deflector to the succeeding output deflector. As a result, the number of adjustment elements (parameters) controlled by the control unit is increased, and thus more accurate control is possible.

In the particle accelerator according to the aspect of the present invention, the control unit may adjust an amount of excitation of the deflection section quadrupole electromagnet of each of the plurality of deflection sections or an amount of excitation of the quadrupole magnetic field generating mechanism for a deflection section and an amount of excitation of the quadrupole electromagnet of each of the plurality of straight sections such that a phase advance of a betatron oscillation of the output beam is 270±45 degrees in a section from the preceding output deflector to the succeeding output deflector, and the control unit may adjust electric field intensity of the preceding output deflector such that the output beam passes through the vicinity of a passage region of the circulating beam in the first deflection section, the output beam passes through a passage region of the circulating beam in the second deflection section or passes through the vicinity of the passage region of the circulating beam in the second deflection section, and the output beam passes through a position spaced apart from a passage region of the circulating beam in third straight section.

In the particle accelerator according to the aspect of the present invention, each of the plurality of straight sections may have the quadrupole electromagnet, and the control unit may adjust the quadrupole electromagnet of each of the plurality of straight sections such that a phase advance of a betatron oscillation of the output beam is 270±45 degrees in a section from the preceding output deflector to the succeeding output deflector.

In the particle accelerator according to the aspect of the present invention, the control unit may adjust the quadrupole electromagnet of each of the plurality of straight sections such that a phase advance of a betatron oscillation of the output beam is 270±45 degrees in a section from the preceding output deflector to the succeeding output deflector, and the control unit may adjust electric field intensity of the preceding output deflector such that the output beam passes through the vicinity of a passage region of the circulating beam in the first deflection section, the output beam passes through a passage region of the circulating beam in the second deflection section or passes through the vicinity of the passage region of the circulating beam in the second deflection section, and the output beam passes through a position spaced apart from a passage region of the circulating beam in third straight section.

In the particle accelerator according to the aspect of the present invention, a deflection angle of the charged particle beam caused by the first deflection section may be 60 degrees or more.

In the particle accelerator according to the aspect of the present invention, a total deflection angle of the charged particle beam caused by the first deflection section and the second deflection section may be 180 degrees.

In the particle accelerator according to the aspect of the present invention, each of the first straight section and the third straight section may have the quadrupole electromagnet, the preceding output deflector may be disposed on a downstream side of the quadrupole electromagnet of the first straight section in the traveling direction of the circulating beam, and the succeeding output deflector may be disposed on a downstream side of the quadrupole electromagnet of the third straight section in the traveling direction of the circulating beam.

In the particle accelerator according to the aspect of the present invention, the quadrupole electromagnet of the first straight section may be disposed substantially at a center of the first straight section in the traveling direction of the circulating beam, and the quadrupole electromagnet of the third straight section may be disposed substantially at a center of the third straight section in the traveling direction of the circulating beam.

According to another aspect of the present invention, there is provided a particle beam therapy apparatus including: the particle accelerator; and an irradiation device that transports the charged particle beam extracted as the output beam from the particle accelerator and irradiates an irradiation target.

Advantageous Effects of Invention

According to the present invention, it is possible to provide a particle accelerator and a particle beam therapy apparatus that can achieve reduction in size.

Specifically, according to the present invention, it is possible to provide a particle accelerator and a particle beam therapy apparatus that can reduce a magnetic field generation region required for a deflection electromagnet of a deflection section, reduce the overall cost associated with the deflection electromagnet, and achieve reduction in size of the particle accelerator.

BRIEF DESCRIPTION OF DRAWINGS

FIG. 2 shows a block diagram showing a part of a configuration of the synchrotron of the first embodiment and the like.

FIG. 11 is a diagram for explaining an ideal two-dimensional cross-sectional distribution or the like of an irradiation beam.

DESCRIPTION OF EMBODIMENTS

Hereinafter, embodiments of a particle accelerator and a particle beam therapy apparatus according to the present invention will be described with reference to the accompanying drawings.

First Embodiment

Figure 1:
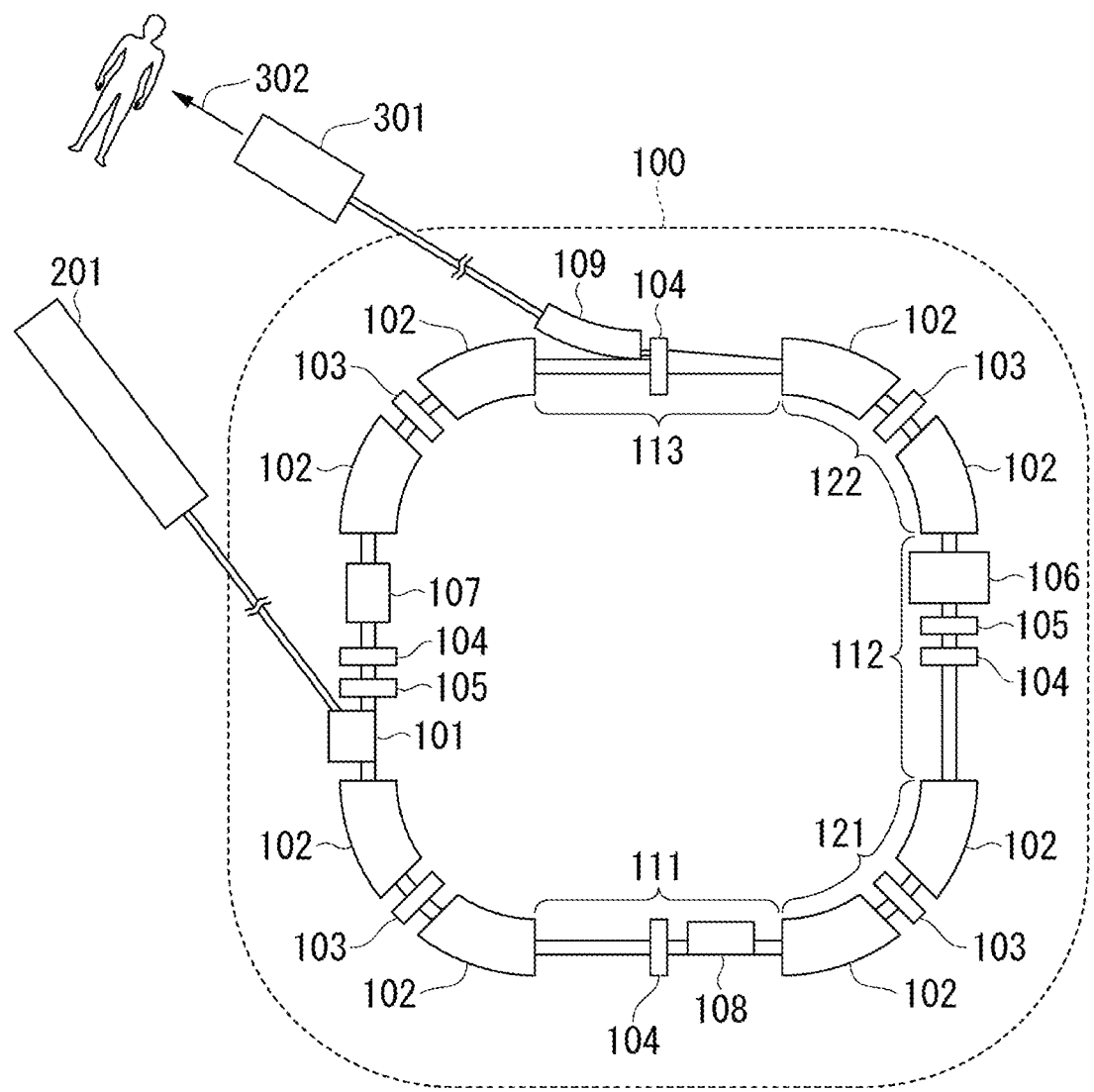
FIG. 1 is a diagram showing an example of a synchrotron (a particle accelerator) according to a first embodiment and a particle beam therapy apparatus to which the synchrotron is applied.
Figure 2:
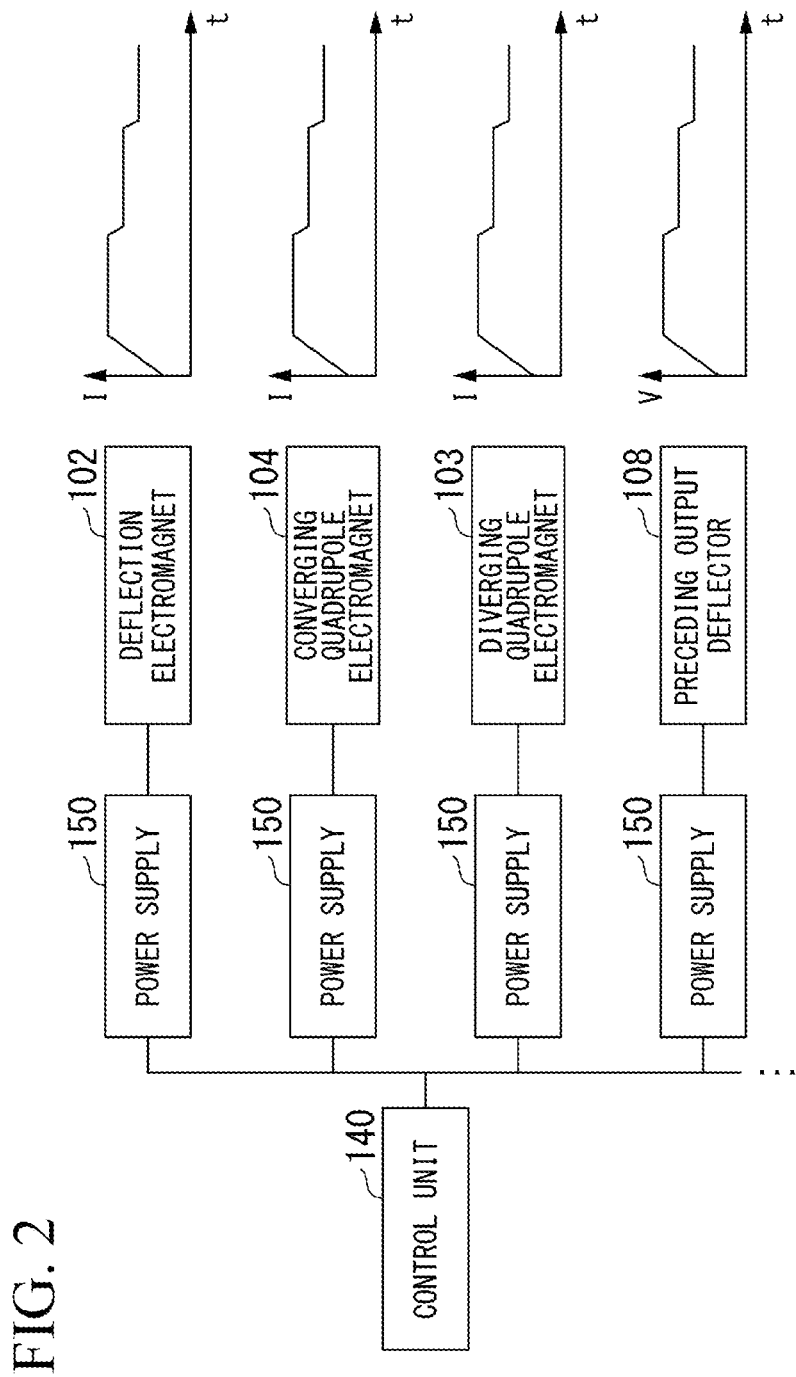

FIG. 1 is a diagram showing an example of a synchrotron (a particle accelerator) 100 according to a first embodiment and a particle beam therapy apparatus to which the synchrotron 100 is applied. FIG. 2 shows a block diagram showing a part of a configuration of the synchrotron 100 of the first embodiment and the like. Specifically, a left part of FIG. 2 shows a part of the configuration of the synchrotron 100 of the first embodiment as a block diagram, the uppermost part on a right side of FIG. 2 shows a relationship between a current I flowing in a deflection electromagnet 102 and a time t, a second part from the top on the right side of FIG. 2 shows a relationship between a current I flowing in a converging quadrupole electromagnet 104 and a time t, a second part from the bottom on the right side of FIG. 2 shows a relationship between a current I flowing in a diverging quadrupole electromagnet 103 and a time t, and the lowermost part on the right side of FIG. 2 shows a relationship between a voltage V between electrodes of a preceding output deflector 108 and a time t.

In the example shown in FIG. 1, the particle beam therapy apparatus to which the synchrotron 100 of the first embodiment is applied includes the synchrotron 100, an injector 201, and an irradiation device 301.

The injector 201 generates charged particles and supplies the charged particles accelerated with predetermined energy to the synchrotron 100. The injector 201 includes, for example, an ion source (not shown) and a linear accelerator (not shown). The ion source generates ions by, for example, colliding high-speed electrons with neutral gas and accelerates the ions in the linear accelerator to be a state where the ions can be accelerated by the synchrotron 100. Atoms or particles to be ionized include, for example, hydrogen, helium, carbon, nitrogen, oxygen, neon, silicon, and argon. The linear accelerator accelerates the charged particles supplied from the ion source with predetermined energy and supplies the charged particles to the synchrotron 100. As a linear accelerator, for example, a radio frequency quadrupole (RFQ) linear accelerator that accelerates and converges the charged particles with a high-frequency quadrupole electric field or a drift tube linear accelerator is used. The charged particles are accelerated by the linear accelerator with energy of several MeV per nucleon, for example.

The irradiation device 301 transports a charged particle beam extracted as an output beam 132 (see FIG. 3) from the synchrotron 100 and irradiates an irradiation target with the charged particle beam as an irradiation beam 302.

In the example shown in FIG. 1, an irradiation field forming device is included in the irradiation device 301, but in another example, the irradiation field forming device and the irradiation device 301 may be provided separately in the particle beam therapy apparatus.

In the example shown in FIGS. 1 and 2, the synchrotron 100 accelerates the charged particle beam supplied from the linear accelerator of the injector 201 while circulating the charged particle beam as a circulating beam 131 and outputs some of the circulating beam 131 as the output beam 132. The synchrotron 100 includes, for example, an injection deflector 101, eight deflection electromagnets 102, four diverging quadrupole electromagnets 103, four converging quadrupole electromagnets 104, two resonance excitation multipole electromagnets 105, a high frequency acceleration cavity 106, a high frequency kicker device 107, a preceding output deflector 108, a succeeding output deflector 109, a control unit 140, and a plurality of power supplies 150.

The injection deflector 101 deflects the charged particle beam injected by the injector 201 to make the charged particle beam into a circulating beam 131. The injection deflector 101 is connected to a first deflection electromagnet 102 disposed on a downstream side thereof in a traveling direction of the circulating beam 131.

The deflection electromagnet 102 deflects the circulating beam 131. The first deflection electromagnet 102 is connected to a first diverging quadrupole electromagnet 103 disposed on a downstream side thereof in the traveling direction of the circulating beam 131.

In the example shown in FIGS. 1 and 2, the deflection electromagnet 102 is not a functionally coupled electromagnet to which a quadrupole magnetic field component is added, but in another example, the deflection electromagnet 102 may be the functionally coupled electromagnet to which a quadrupole magnetic field component is added.

Further, in the example shown in FIGS. 1 and 2, an end portion of the deflection electromagnet 102 has no edge angle, but in other examples, the end portion of the deflection electromagnet 102 may have an edge angle.

Figure 3:
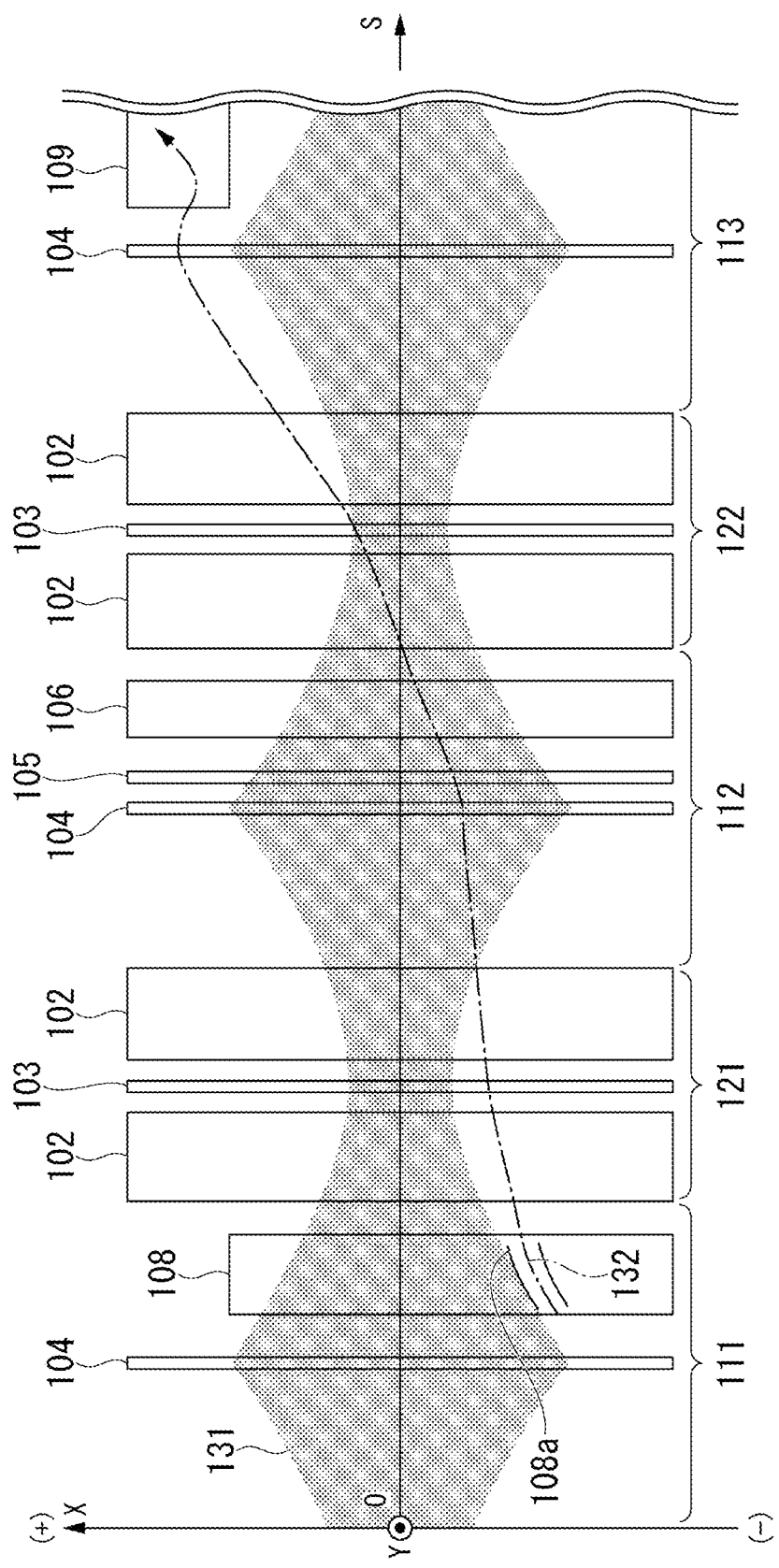
FIG. 3 is a diagram showing a relationship between a passage region of a circulating beam and a trajectory of an output beam in the synchrotron of the first embodiment.

In the example shown in FIGS. 1 and 2, the diverging quadrupole electromagnet 103 causes the circulating beam 131 to diverge in a horizontal direction (an X-axis direction in FIG. 3) and converge in a vertical direction (a Y-axis direction in FIG. 3). The first diverging quadrupole electromagnet 103 is connected to a second deflection electromagnet 102 disposed on a downstream side thereof in the traveling direction of the circulating beam 131. The second deflection electromagnet 102 is connected to a first converging quadrupole electromagnet 104 disposed on a downstream side thereof in the traveling direction of the circulating beam 131.

The converging quadrupole electromagnet 104 causes the circulating beam 131 to converge in the horizontal direction and diverge in the vertical direction. The first converging quadrupole electromagnet 104 is connected to the preceding output deflector 108 disposed on a downstream side thereof in the traveling direction of the circulating beam 131.

The preceding output deflector 108 includes a septum electrode 108a (see FIG. 3). The septum electrode 108a deflects some of the circulating beam 131 toward an inner side of a circulating trajectory (a hatched portion in FIG. 3) of the circulating beam 131 (a negative side on an X axis in FIG. 3 with respect to the circulating trajectory of the circulating beam 131) to separate the some of the circulating beam 131 as the output beams 132.

In the example shown in FIGS. 1 and 2, the output beam 132 is bent to be separated from the circulating beam 131 by the preceding output deflector 108 which is an electrostatic device constituted by the septum electrode 108a formed thin to minimize beam loss.

As shown in FIG. 1, the first converging quadrupole electromagnet 104 and the preceding output deflector 108 are provided in a first straight section 111. The first converging quadrupole electromagnet 104 is disposed substantially at a center of the first straight section 111 in the traveling direction of the circulating beam 131. The first straight section 111 does not have the deflection electromagnet 102.

In the example shown in FIG. 1, the first converging quadrupole electromagnet 104 is disposed substantially at the center of the first straight section 111 in the traveling direction of the circulating beam 131, and thus a beam passage region of a first deflection section 121 in which the circulating beam 131 and the output beam 132 are mixed can be reduced, and a magnetic field generation region necessary for the deflection electromagnet 102 of the first deflection section 121 can be minimized.

In another example, the first converging quadrupole electromagnet 104 may not be disposed substantially at the center of the first straight section 111 in the traveling direction of the circulating beam 131. In still another example, the first converging quadrupole electromagnet 104 may not be disposed in the first straight section 111.

Figure 15:
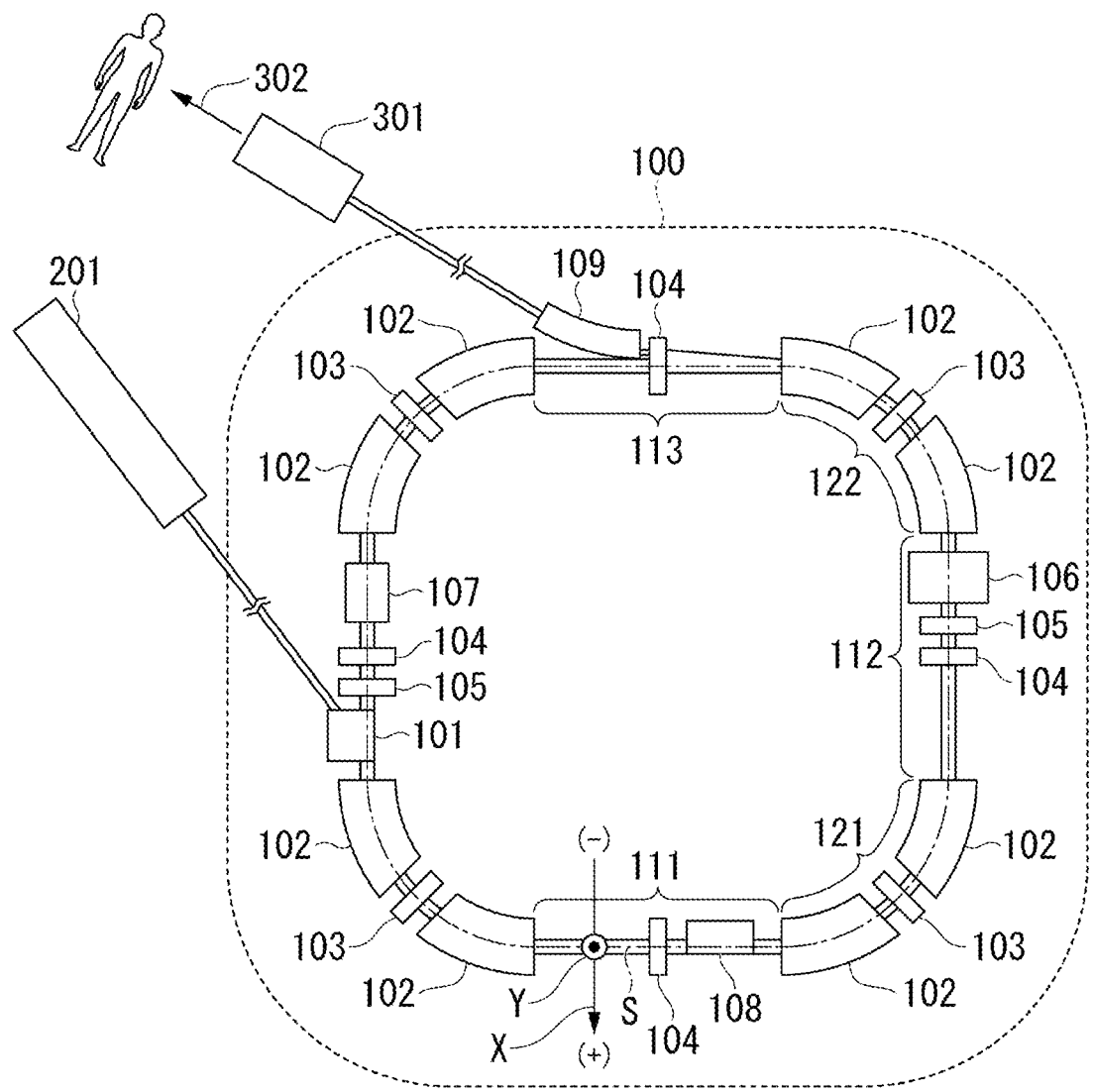
FIG. 15 is a diagram obtained by relating FIG. 1 and FIG. 3 with each other.

FIG. 3 is a diagram showing a relationship between a passage region of the circulating beam 131 and a trajectory of the output beam 132 in the synchrotron (the particle accelerator) 100 of the first embodiment. In FIG. 3, an S-axis direction indicates the traveling direction of the circulating beam 131. An X axis included in a plane orthogonal to an S axis corresponds to a deflection direction of the deflection electromagnet 102, a deflection direction of the preceding output deflector 108, and a deflection direction of the succeeding output deflector 109. FIG. 15 is a diagram obtained by relating FIG. 1 and FIG. 3 with each other.

The deflection directions of the deflection electromagnet 102, the preceding output deflector 108, and the succeeding output deflector 109 are all the same axial direction in an XYS coordinate system, and a positive and a negative of the deflection directions are different from each other. The X axis is parallel to the deflection direction of the deflection electromagnet 102, the deflection direction of the preceding output deflector 108, and the deflection direction of the succeeding output deflector 109. A Y axis included in the plane orthogonal to the S axis is orthogonal to the X axis.

Here, in FIG. 3, an intersection point of the X axis, the Y axis, and the S axis is indicated as O. Although not particularly limited, the outer side of the circulating trajectory of the circulating beam 131 in the synchrotron 100 is indicated as a positive (+) on the X axis, and the inner side of the circulating trajectory of the circulating beam 131 is indicated as a negative (−) on the X axis.

As shown in FIG. 3, the circulating beam 131 is caused to converge by the first converging quadrupole electromagnet 104, and then some of the circulating beam 131 is deflected toward the inner side of the circulating trajectory (the hatched portion in FIG. 3) of the circulating beam 131 (a lower side in FIG. 3 with respect to the circulating trajectory of the circulating beam 131) by the septum electrode 108a of the preceding output deflector 108 to be separated as the output beam 132.

In the example shown in FIGS. 1 to 3, the preceding output deflector 108 is connected to a third deflection electromagnet 102 disposed on a downstream side thereof in the traveling direction of the circulating beam 131. The third deflection electromagnet 102 is connected to a second diverging quadrupole electromagnet 103 disposed on a downstream side thereof in the traveling direction of the circulating beam 131. The second diverging quadrupole electromagnet 103 is connected to a fourth deflection electromagnet 102 disposed on a downstream side thereof in the traveling direction of the circulating beam 131.

As shown in FIGS. 1 and 3, the third deflection electromagnet 102, the second diverging quadrupole electromagnet 103, and the fourth deflection electromagnet 102 are provided in the first deflection section 121.

In the example shown in FIGS. 1 to 3, two deflection electromagnets 102 are provided in the first deflection section 121, but in another example, three or more deflection electromagnets 102 may be provided in the first deflection section 121.

In the example shown in FIGS. 1 to 3, one diverging quadrupole electromagnet 103 constituting a short straight section is provided in the first deflection section 121, but in another example, two or more quadrupole electromagnets (a diverging quadrupole electromagnet may not be used) may be provided in the first deflection section 121.

In still another example, a quadrupole magnetic field generating mechanism for a deflection section obtained by integrating the deflection electromagnet 102 and a quadrupole magnetic field coil may be provided in the first deflection section 121.

In the example shown in FIGS. 1 to 3, the fourth deflection electromagnet 102 is connected to a second converging quadrupole electromagnet 104 disposed on a downstream side thereof in the traveling direction of the circulating beam 131. The second converging quadrupole electromagnet 104 is connected to a first resonance excitation multipole electromagnet 105 disposed on a downstream side thereof in the traveling direction of the circulating beam 131. The first resonance excitation multipole electromagnet 105 is connected to the high frequency acceleration cavity 106 disposed on a downstream side thereof in the traveling direction of the circulating beam 131.

As shown in FIGS. 1 and 3, the second converging quadrupole electromagnet 104, the first resonance excitation multipole electromagnet 105, and the high frequency acceleration cavity 106 are provided in a second straight section 112. The second straight section 112 does not have the deflection electromagnet 102.

In the example shown in FIGS. 1 to 3, the second converging quadrupole electromagnet 104 is disposed substantially at a center of the second straight section 112 in the traveling direction of the circulating beam 131, and thus a beam passage region of a second deflection section 122 in which the circulating beam 131 and the output beam 132 are mixed can be reduced, and a magnetic field generation region necessary for the deflection electromagnet 102 of the second deflection section 122 can be minimized.

In another example, the second converging quadrupole electromagnet 104 may not be disposed substantially at the center of the second straight section 112 in the traveling direction of the circulating beam 131. In still another example, the second converging quadrupole electromagnet 104 may not be disposed in the second straight section 112.

In the example shown in FIGS. 1 to 3, the high frequency acceleration cavity 106 is connected to a fifth deflection electromagnet 102 disposed on a downstream side thereof in the traveling direction of the circulating beam 131. The fifth deflection electromagnet 102 is connected to a third diverging quadrupole electromagnet 103 disposed on a downstream side thereof in the traveling direction of the circulating beam 131. The third diverging quadrupole electromagnet 103 is connected to a sixth deflection electromagnet 102 disposed on a downstream side thereof in the traveling direction of the circulating beam 131.

As shown in FIGS. 1 and 3, the fifth deflection electromagnet 102, the third diverging quadrupole electromagnet 103, and the sixth deflection electromagnet 102 are provided in the second deflection section 122.

In the example shown in FIGS. 1 to 3, two deflection electromagnets 102 are provided in the second deflection section 122, but in another example, three or more deflection electromagnets 102 may be provided in the second deflection section 122.

In the example shown in FIGS. 1 to 3, one diverging quadrupole electromagnet 103 constituting a short straight section is provided in the second deflection section 122, but in another example, two or more quadrupole electromagnets (a diverging quadrupole electromagnet may not be used) may be provided in the second deflection section 122.

In still another example, a quadrupole magnetic field generating mechanism for a deflection section obtained by integrating the deflection electromagnet 102 and a quadrupole magnetic field coil may be provided in the second deflection section 122.

In the example shown in FIGS. 1 to 3, the sixth deflection electromagnet 102 is connected to a third converging quadrupole electromagnet 104 disposed on a downstream side thereof in the traveling direction of the circulating beam 131. The third converging quadrupole electromagnet 104 is connected to the succeeding output deflector 109 disposed on a downstream side thereof in the traveling direction of the circulating beam 131.

The succeeding output deflector 109 deflects the output beam 132 separated from the circulating beam 131 by the preceding output deflector 108 toward the outer side of the circulating trajectory of the circulating beam 131 (a positive side on the X axis in FIG. 3).

As shown in FIG. 3, the output beam 132 is deflected toward the outer side (an upper side in FIG. 3) of the circulating trajectory (the hatched portion in FIG. 3) of the circulating beam 131 by the succeeding output deflector 109.

As shown in FIGS. 1 and 3, the third converging quadrupole electromagnet 104 and the succeeding output deflector 109 are provided in a third straight section 113. The third converging quadrupole electromagnet 104 is disposed substantially at a center of the third straight section 113 in the traveling direction of the circulating beam 131. The third straight section 113 does not have the deflection electromagnet 102.

In the example shown in FIGS. 1 to 3, a septum electromagnet that deflects the output beam 132 in the X-axis direction is used in the succeeding output deflector 109, but in another example, a Lambertson-type electromagnet that deflects the output beam 132 in the Y-axis direction may be used in the succeeding output deflector 109.

In the example shown in FIGS. 1 to 3, the third converging quadrupole electromagnet 104 is connected to a seventh deflection electromagnet 102 disposed on a downstream side thereof in the traveling direction of the circulating beam 131. The seventh deflection electromagnet 102 is connected to a fourth diverging quadrupole electromagnet 103 disposed on a downstream side thereof in the traveling direction of the circulating beam 131. The fourth diverging quadrupole electromagnet 103 is connected to an eighth deflection electromagnet 102 disposed on a downstream side thereof in the traveling direction of the circulating beam 131.

The eighth deflection electromagnet 102 is connected to the high frequency kicker device 107 disposed on a downstream side thereof in the traveling direction of the circulating beam 131. The high frequency kicker device 107 is connected to a fourth converging quadrupole electromagnet 104 disposed on a downstream side thereof in the traveling direction of the circulating beam 131. The fourth converging quadrupole electromagnet 104 is connected to a second resonance excitation multipole electromagnet 105 disposed on a downstream side thereof in the traveling direction of the circulating beam 131. The second resonance excitation multipole electromagnet 105 is connected to the injection deflector 101 disposed on a downstream side thereof in the traveling direction of the circulating beam 131.

In the example shown in FIGS. 1 to 3, the synchrotron 100 includes the first straight section 111, the first deflection section 121, the second straight section 112, the second deflection section 122, and the third straight section 113. The second straight section 112 is disposed on a downstream side of the first straight section 111 in the traveling direction of the circulating beam 131, and the third straight section 113 is disposed on a downstream side of the second straight section 112 in the traveling direction of the circulating beam 131. The first deflection section 121 connects the first straight section 111 and the second straight section 112 to each other, and the second deflection section 122 connects the second straight section 112 and the third straight section 113 to each other.

As shown in FIG. 1, the first straight section 111 and the third straight section 113 are disposed at positions facing each other on the circulating trajectory of the circulating beam 131. As a result, symmetry can be maintained in a case where the first straight section 111 and the third straight section 113 extend.

Further, the first straight section 111 and the third straight section 113 extend parallel to each other. As a result, a minimum of symmetry can be maintained.

Each of the eight deflection electromagnets 102 is controlled by the control unit 140 via a power supply 150. Each of the four converging quadrupole electromagnets 104 is controlled by the control unit 140 via a power supply 150. Each of the four diverging quadrupole electromagnets 103 is controlled by the control unit 140 via a power supply 150. The preceding output deflector 108 is controlled by the control unit 140 via a power supply 150. Although not shown in FIG. 2, the succeeding output deflector 109 is also controlled by the control unit 140 via a power supply 150.

A horizontal spread of the circulating beam 131 (that is, a spread in a plane including the X axis and the S axis in FIG. 3) $\sigma_x(s)$ is represented by the following Equation (1). In Equation (1), $\beta$ is a betatron amplitude function, $\varepsilon$ is a beam emittance, D is a momentum dispersion function, and $\Delta p/p$ indicates a momentum spread of a beam.

$$\sigma_x(S) = \sqrt{\beta_x(S) \cdot \varepsilon_x + \left(D_x(S) \cdot \frac{\Delta p}{p}\right)^2} \quad [\text{Math. 1}]$$

A phase advance $\Delta \mu_x$ [rad] of a betatron oscillation is represented by the following Equation (2). In Equation (2), $S_1$ indicates a position of an entrance of the preceding output deflector 108 in the traveling direction (the S-axis direction) of the circulating beam 131, and $S_2$ indicates a position an entrance of the succeeding output deflector 109 in the traveling direction of the circulating beam 131 (the S-axis direction).

$$\Delta \mu_x = \mu_x(S_2) - \mu_x(S_1) = \int_{S_1}^{S_2} \frac{ds}{\beta_x(S)} \quad [\text{Math. 2}]$$

Figure 4:
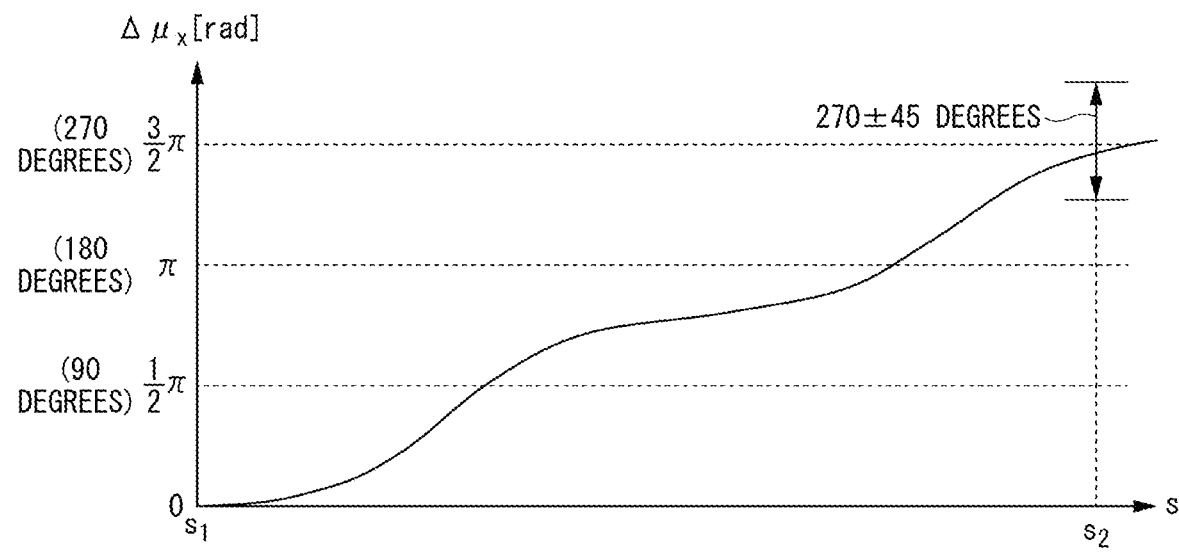
FIG. 4 is a diagram showing an example of a phase advance of a betatron oscillation of the output beam set in the synchrotron of the first embodiment.

FIG. 4 is a diagram showing an example of a phase advance of a betatron oscillation of the output beam 132 set in the synchrotron (the particle accelerator) 100 of the first embodiment. In FIG. 4, a vertical axis indicates a phase advance $\Delta \mu_x$ [rad] of a betatron oscillation, and a horizontal axis indicates a position S in the traveling direction of the circulating beam 131 (the S-axis direction).

As shown in FIG. 4, in the synchrotron (the particle accelerator) 100 of the first embodiment, a phase advance of a betatron oscillation of the output beam 132 (specifically, a phase advance of a betatron oscillation of the output beam 132 in a movement axis direction which is the same as the deflection direction of the preceding output deflector 108 (the X-axis direction in FIG. 3) is set to be 270±45 degrees in a section from the preceding output deflector 108 to the succeeding output deflector 109.

Specifically, the control unit 140 controls the diverging quadrupole electromagnet 103 and the converging quadrupole electromagnet 104 such that a phase advance of a betatron oscillation of the output beam 132 is 270±45 degrees in a section from the preceding output deflector 108 to the succeeding output deflector 109. Next (or at the same time), as shown in FIG. 3, the control unit 140 controls the preceding output deflector 108 such that the output beam 132 passes through the vicinity of a passage region (the hatched portion in FIG. 3) of the circulating beam 131 in the first deflection section 121, the output beam 132 passes through a passage region of the circulating beam 131 in the second deflection section 122 or passes through the vicinity of the passage region of the circulating beam 131 in the second deflection section 122, and the output beam 132 passes through a position spaced apart from a passage region of the circulating beam 131 in third straight section 113.

Specifically, the control unit 140 adjusts an amount of excitation of the diverging quadrupole electromagnet 103 and an amount of excitation of the converging quadrupole electromagnet 104 via the power supply 150 such that a phase advance of a betatron oscillation of the output beam 132 is 270±45 degrees in a section from the preceding output deflector 108 to the succeeding output deflector 109.

In parallel with this, as shown in FIG. 3, the control unit 140 adjusts electric field intensity of the preceding output deflector 108 via the power supply 150 such that the output beam 132 passes through the vicinity of a passage region (the hatched portion in FIG. 3) of the circulating beam 131 in the first deflection section 121, the output beam 132 passes through a passage region of the circulating beam 131 in the second deflection section 122 or passes through the vicinity of the passage region of the circulating beam 131 in the second deflection section 122, and the output beam 132 passes through a position spaced apart from a passage region of the circulating beam 131 in third straight section 113.

Further, in the synchrotron (the particle accelerator) 100 of the first embodiment, a deflection angle of the charged particle beam caused by the first deflection section 121 is 60 degrees or more. Preferably, a deflection angle of the charged particle beam caused by the first deflection section 121 is 90 degrees or more. Therefore, the deflection electromagnet 102 can work as a strong converging element. Furthermore, in the synchrotron (the particle accelerator) 100 of the first embodiment, a total deflection angle of the charged particle beam caused by the first deflection section 121 and the second deflection section 122 is 180 degrees.

In the example shown in FIGS. 1 to 4, some of the circulating beam 131 is deflected toward the inner side of the circulating trajectory (the hatched portion in FIG. 3) of the circulating beam 131 (the negative side on the X axis in FIG. 3 with respect to the circulating trajectory of the circulating beam 131) to be separated as the output beam 132 in the preceding output deflector 108.

In another example, some of the circulating beam 131 may be deflected toward the outer side of the circulating trajectory (the hatched portion in FIG. 3) of the circulating beam 131 (the positive side on the X axis in FIG. 3 with respect to the circulating trajectory of the circulating beam 131) to be separated as the output beam 132 in the preceding output deflector 108. In this example, the output beam 132 separated from the circulating beam 131 by the preceding output deflector 108 is deflected toward the inner side of the circulating trajectory of the circulating beam 131 (a negative side on the X axis in FIG. 3), in the succeeding output deflector 109.

In the synchrotron (the particle accelerator) 100 of the first embodiment, as shown in FIG. 1, since the succeeding output deflector 109 is disposed in the third straight section 113, it is possible to realize the trajectory of the output beam 132 shown in FIG. 3 without requiring a large expansion of the magnetic field generation regions of the deflection electromagnets 102 of the deflection sections 121 and 122, and it is possible to reduce a size of the deflection electromagnet 102.

Figure 10:
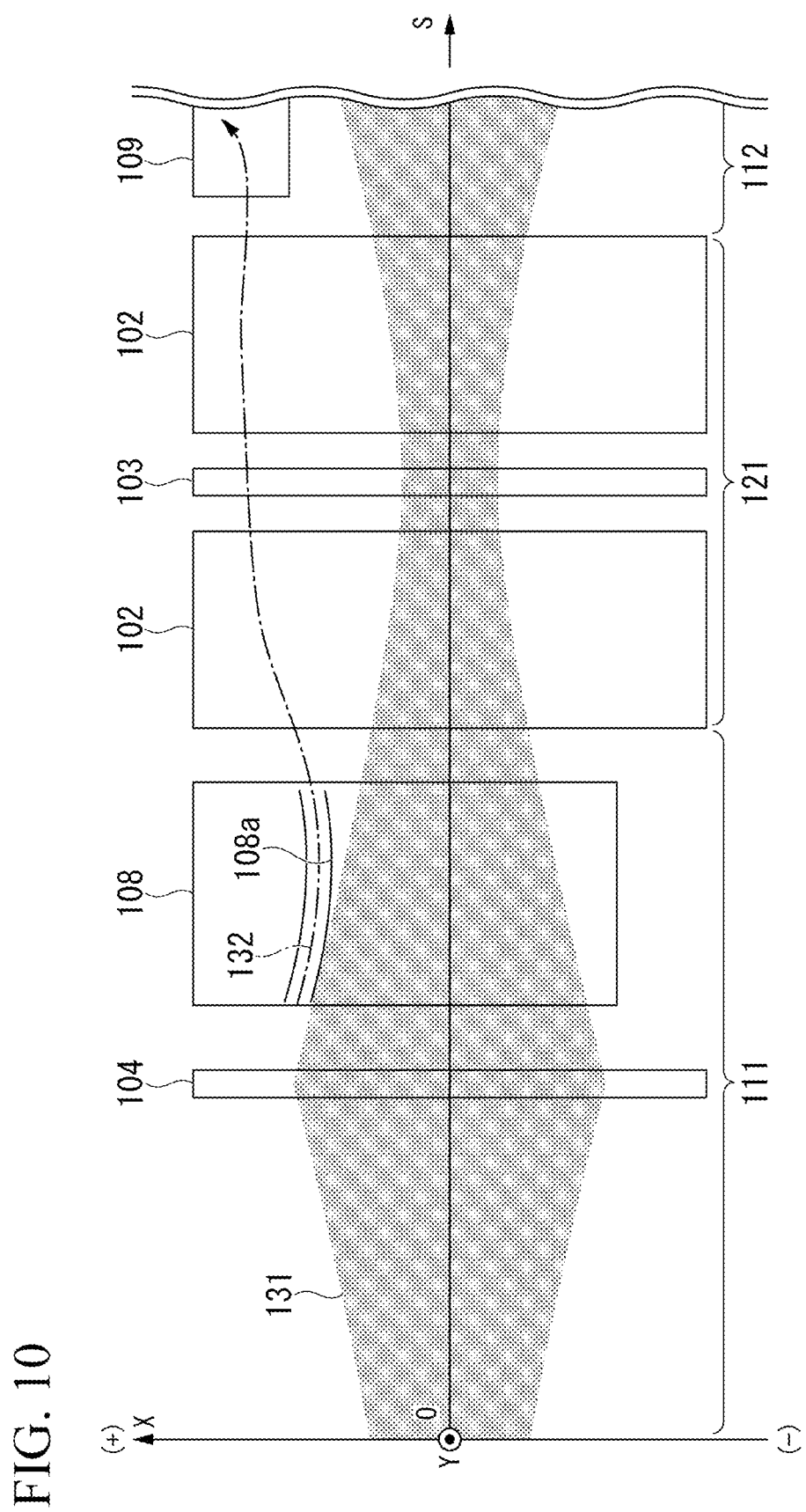
FIG. 10 is a diagram showing a relationship between a passage region of a circulating beam and a trajectory of an output beam in an example of the related art shown in FIG. 9.

Further, in the synchrotron (the particle accelerator) 100 of the first embodiment, the output beam 132 is bent to be separated from the circulating beam 131 by the preceding output deflector 108 which is an electrostatic device constituted by the septum electrode 108a formed thin to minimize beam loss and enters the first deflection section 121. In the first deflection section 121, the trajectory of the output beam 132 does not largely deviate from the passage region (the hatched portion in FIGS. 3 and 10) of the circulating beam 131 as in the example of the related art shown in FIG. 10 and follows a contour of the passage region of the circulating beam 131. Therefore, a magnetic field region generated by the deflection electromagnet 102, which is widened for the output beam 132, can also be curbed to a minimum range.

Similarly, the trajectory of the output beam 132 in the second deflection section 122 after passing through the second straight section 112 follows the contour of the passage region of the circulating beam 131.

In each example of the synchrotron 100 of the first embodiment, an amount of excitation of the diverging quadrupole electromagnet 103 and/or an amount of excitation of the converging quadrupole electromagnet 104 is adjusted such that a phase advance of a betatron oscillation of the output beam 132 is 270±45 degrees in a section from the preceding output deflector 108 to the succeeding output deflector 109. Therefore, in each example of the synchrotron 100 of the first embodiment, the output beam 132 is largely separated from the circulating beam 131 in the third straight section 113 and is extracted to the outside from the synchrotron 100 without loss by the succeeding output deflector 109 which is a septum electromagnet.

In the synchrotron 100 of the first embodiment, since the output beam 132 passing through the deflection sections 121 and 122 does not pass through a position spaced apart from a center of the deflection electromagnet 102 for a very long time, the output beam 132 is not greatly affected by a nonlinear magnetic field component of the deflection electromagnet 102 unlike the example of the related art shown in FIG. 11(B). Therefore, the irradiation beam 302 which is extracted from the synchrotron 100 of the first embodiment and is emitted to the irradiation target from the irradiation device 301 including the irradiation field forming device has a shape of a two-dimensional cross-sectional distribution close to that of the ideal two-dimensional cross-sectional distribution 302a as shown in FIG. 11(A), and high dose accuracy can be maintained.

As described above, in the synchrotron 100 of the first embodiment, since a phase of a betatron oscillation of the output beam 132 and an arrangement of an output device are optimized, it is possible to realize a trajectory of the output beam 132 through which the output beam 132 can be transported without loss in a magnetic field generation region equal to the passage region of the circulating beam 131, it is possible to greatly reduce the magnetic field generation region required for the deflection electromagnet 102, and it is possible to reduce the overall cost related to the deflection electromagnet 102.

Further, in the synchrotron 100 of the first embodiment, as shown in FIG. 3, the output beam 132 has a trajectory that does not largely deviate from the passage region (the hatched portion in FIG. 3) of the circulating beam 131 in the first deflection section 121, has a trajectory that obliquely crosses a central trajectory (the hatched portion in FIG. 3) of the circulating beam 131 in the second straight section 112, and has a trajectory that does not largely deviate from the passage region (the hatched portion in FIG. 3) of the circulating beam 131 in the second deflection section 122.

Further, the circulating beam 131 and the output beam 132 are largely separated in the third straight section 113 in which the succeeding output deflector 109 is disposed. Therefore, in the synchrotron 100 of the first embodiment, it is possible to extract the output beam 132 from the synchrotron 100 without loss without greatly widening the magnetic field generation regions of the deflection electromagnets 102 of the deflection sections 121 and 122.

In other words, in the synchrotron 100 of the first embodiment, it is possible to realize reduction in size of the synchrotron 100 without requiring a large expansion of the magnetic field generation regions of the deflection electromagnets 102 of the deflection sections 121 and 122. In particular, in a case where a superconductive electromagnet is used as the deflection electromagnet 102, the manufacturing difficulty, the manufacturing cost, and the operating cost of the deflection electromagnet 102 can be curbed.

Second Embodiment

Hereinafter, a particle accelerator and a particle beam therapy apparatus according to a second embodiment of the present invention will be described.

The particle accelerator (a synchrotron 100) of the second embodiment has the same configuration as the particle accelerator (the synchrotron 100) of the above-described first embodiment except for points which will be described later. Therefore, according to the particle accelerator (the synchrotron 100) of the second embodiment, the same effects as the particle accelerator (the synchrotron 100) of the above-described first embodiment can be exhibited except for the points which will be described later.

Figure 5:
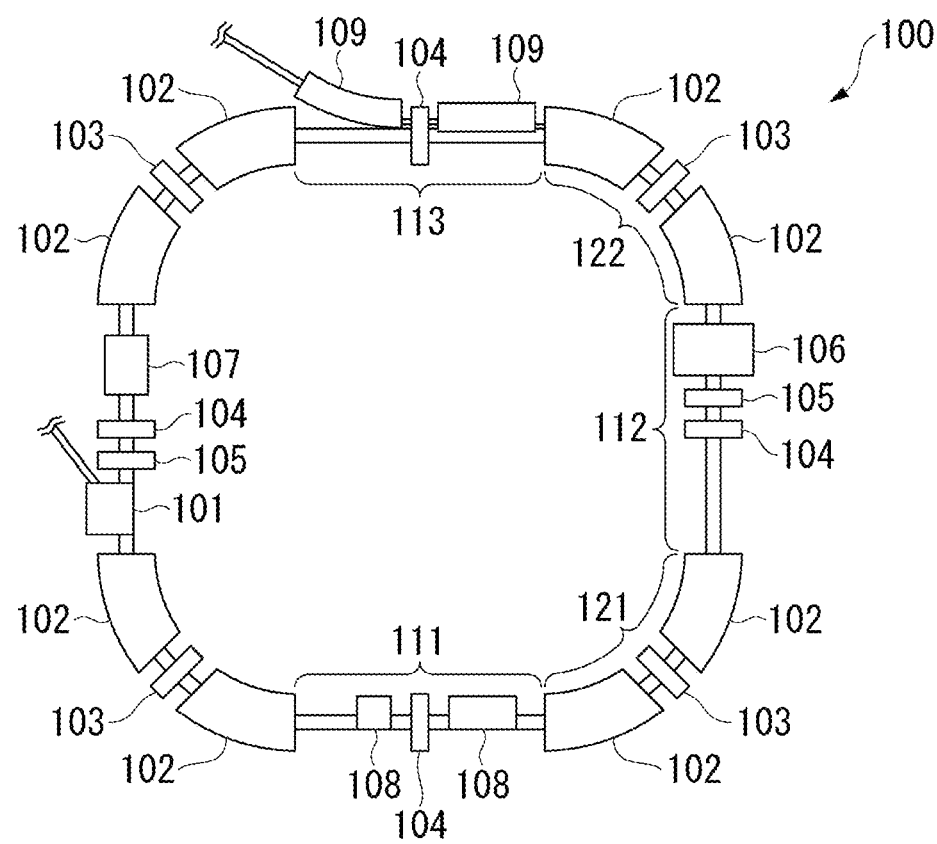
FIG. 5 is a diagram showing an example of a synchrotron (a particle accelerator) according to a second embodiment.

FIG. 5 is a diagram showing an example of the synchrotron (the particle accelerator) 100 according to the second embodiment.

In the example shown in FIG. 5, the synchrotron 100 accelerates the charged particle beam supplied from the linear accelerator of the injector 201 (see FIG. 1) while circulating the charged particle beam as a circulating beam 131 and outputs some of the circulating beam 131 as an output beam 132. The synchrotron 100 includes, for example, an injection deflector 101, eight deflection electromagnets 102, four diverging quadrupole electromagnets 103, four converging quadrupole electromagnets 104, two resonance excitation multipole electromagnets 105, a high frequency acceleration cavity 106, a high frequency kicker device 107, two preceding output deflectors 108, two succeeding output deflectors 109, a control unit 140 (see FIG. 2), and a plurality of power supplies 150 (see FIG. 2).

In other words, in the example shown in FIG. 5, one unit of the preceding output deflector 108 and one unit of the succeeding output deflector 109 are added as compared with the example shown in FIG. 1.

A high-intensity electromagnetic field is required to bend a charged particle beam that has been accelerated with high energy, but it is practically difficult to raise the intensity beyond the above configuration due to the discharge limit of the vacuum, magnetic flux saturation of an iron core, and the like. In such cases, it is common to increase an effective deflection angle by extending a device length of the output deflector, but the device length cannot be extended further as it is if other devices are close to the front and back thereof. It is conceivable to extend the straight sections 111 and 113 themselves to create a space for extending the device length, but this is not desirable in aiming to reduce the size of the synchrotron 100. Even under such conditions, in the example shown in FIG. 5, each of the preceding output deflector 108 and the succeeding output deflector 109 is configured as two units to straddle another device (the converging quadrupole electromagnet 104), and thus the deflection angle with respect to the output beam 132 can be increased without extending the straight sections 111 and 113.

In the example shown in FIG. 5, the injection deflector 101 has the same function as the injection deflector 101 shown in FIG. 1. The injection deflector 101 is connected to a first deflection electromagnet 102 disposed on a downstream side thereof in a traveling direction of the circulating beam 131.

The deflection electromagnet 102 has the same function as the deflection electromagnet 102 shown in FIG. 1. The first deflection electromagnet 102 is connected to a first diverging quadrupole electromagnet 103 disposed on a downstream side thereof in the traveling direction of the circulating beam 131.

The diverging quadrupole electromagnet 103 has the same function as the diverging quadrupole electromagnet 103 shown in FIG. 1. The first diverging quadrupole electromagnet 103 is connected to a second deflection electromagnet 102 disposed on a downstream side thereof in the traveling direction of the circulating beam 131. The second deflection electromagnet 102 is connected to a first preceding output deflector 108 disposed on a downstream side thereof in the traveling direction of the circulating beam 131.

Each of the two preceding output deflectors 108 has the same function as the preceding output deflector 108 shown in FIG. 1. The first preceding output deflector 108 is connected to a first converging quadrupole electromagnet 104 disposed on a downstream side thereof in the traveling direction of the circulating beam 131.

The converging quadrupole electromagnet 104 has the same function as the converging quadrupole electromagnet 104 shown in FIG. 1. The first converging quadrupole electromagnet 104 is connected to a second preceding output deflector 108 disposed on a downstream side thereof in the traveling direction of the circulating beam 131.

As shown in FIG. 5, the first preceding output deflector 108, the first converging quadrupole electromagnet 104, and the second preceding output deflector 108 are provided in a first straight section 111. The first converging quadrupole electromagnet 104 is disposed substantially at a center of the first straight section 111 in the traveling direction of the circulating beam 131. The first straight section 111 does not have the deflection electromagnet 102.

In another example, three or more preceding output deflectors 108 may be provided in the first straight section 111. In still another example, either one of the first preceding output deflector 108 and the second preceding output deflector 108 may not be provided in the first straight section 111.

In the example shown in FIG. 5, the second preceding output deflector 108 is connected to a third deflection electromagnet 102 disposed on a downstream side thereof in the traveling direction of the circulating beam 131. The third deflection electromagnet 102 is connected to a second diverging quadrupole electromagnet 103 disposed on a downstream side thereof in the traveling direction of the circulating beam 131. The second diverging quadrupole electromagnet 103 is connected to a fourth deflection electromagnet 102 disposed on a downstream side thereof in the traveling direction of the circulating beam 131.

As shown in FIG. 5, the third deflection electromagnet 102, the second diverging quadrupole electromagnet 103, and the fourth deflection electromagnet 102 are provided in a first deflection section 121.

In another example, a quadrupole magnetic field generating mechanism for a deflection section obtained by integrating the deflection electromagnet 102 and a quadrupole magnetic field coil may be provided in the first deflection section 121.

In the example shown in FIG. 5, the fourth deflection electromagnet 102 is connected to a second converging quadrupole electromagnet 104 disposed on a downstream side thereof in the traveling direction of the circulating beam 131. The second converging quadrupole electromagnet 104 is connected to a first resonance excitation multipole electromagnet 105 disposed on a downstream side thereof in the traveling direction of the circulating beam 131. The first resonance excitation multipole electromagnet 105 is connected to the high frequency acceleration cavity 106 disposed on a downstream side thereof in the traveling direction of the circulating beam 131.

As shown in FIG. 5, the second converging quadrupole electromagnet 104, the first resonance excitation multipole electromagnet 105, and the high frequency acceleration cavity 106 are provided in a second straight section 112. The second straight section 112 does not have the deflection electromagnet 102.

In the example shown in FIG. 5, the high frequency acceleration cavity 106 is connected to a fifth deflection electromagnet 102 disposed on a downstream side thereof in the traveling direction of the circulating beam 131. The fifth deflection electromagnet 102 is connected to a third diverging quadrupole electromagnet 103 disposed on a downstream side thereof in the traveling direction of the circulating beam 131. The third diverging quadrupole electromagnet 103 is connected to a sixth deflection electromagnet 102 disposed on a downstream side thereof in the traveling direction of the circulating beam 131.

As shown in FIG. 5, the fifth deflection electromagnet 102, the third diverging quadrupole electromagnet 103, and the sixth deflection electromagnet 102 are provided in a second deflection section 122.

In another example, a quadrupole magnetic field generating mechanism for a deflection section obtained by integrating the deflection electromagnet 102 and a quadrupole magnetic field coil may be provided in the second deflection section 122.

In the example shown in FIG. 5, the sixth deflection electromagnet 102 is connected to a first succeeding output deflector 109 disposed on a downstream side thereof in the traveling direction of the circulating beam 131.

Each of the two succeeding output deflectors 109 has the same function as the succeeding output deflector 109 shown in FIG. 1. The first succeeding output deflector 109 is connected to a third converging quadrupole electromagnet 104 disposed on a downstream side thereof in the traveling direction of the circulating beam 131.

The third converging quadrupole electromagnet 104 is connected to a second succeeding output deflector 109 disposed on a downstream side thereof in the traveling direction of the circulating beam 131.

As shown in FIG. 5, the first succeeding output deflector 109, the third converging quadrupole electromagnet 104, and the second succeeding output deflector 109 are provided in a third straight section 113. The third converging quadrupole electromagnet 104 is disposed substantially at a center of the third straight section 113 in the traveling direction of the circulating beam 131. The third straight section 113 does not have the deflection electromagnet 102.

In another example, three or more succeeding output deflectors 109 may be provided in the third straight section 113. In still another example, either one of the first succeeding output deflector 109 and the second succeeding output deflector 109 may not be provided in the third straight section 113.

In the example shown in FIG. 5, the third converging quadrupole electromagnet 104 is connected to a seventh deflection electromagnet 102 disposed on a downstream side thereof in the traveling direction of the circulating beam 131. The seventh deflection electromagnet 102 is connected to a fourth diverging quadrupole electromagnet 103 disposed on a downstream side thereof in the traveling direction of the circulating beam 131. The fourth diverging quadrupole electromagnet 103 is connected to an eighth deflection electromagnet 102 disposed on a downstream side thereof in the traveling direction of the circulating beam 131.

The eighth deflection electromagnet 102 is connected to the high frequency kicker device 107 disposed on a downstream side thereof in the traveling direction of the circulating beam 131. The high frequency kicker device 107 is connected to a fourth converging quadrupole electromagnet 104 disposed on a downstream side thereof in the traveling direction of the circulating beam 131. The fourth converging quadrupole electromagnet 104 is connected to a second resonance excitation multipole electromagnet 105 disposed on a downstream side thereof in the traveling direction of the circulating beam 131. The second resonance excitation multipole electromagnet 105 is connected to the injection deflector 101 disposed on a downstream side thereof in the traveling direction of the circulating beam 131.

Figure 14:
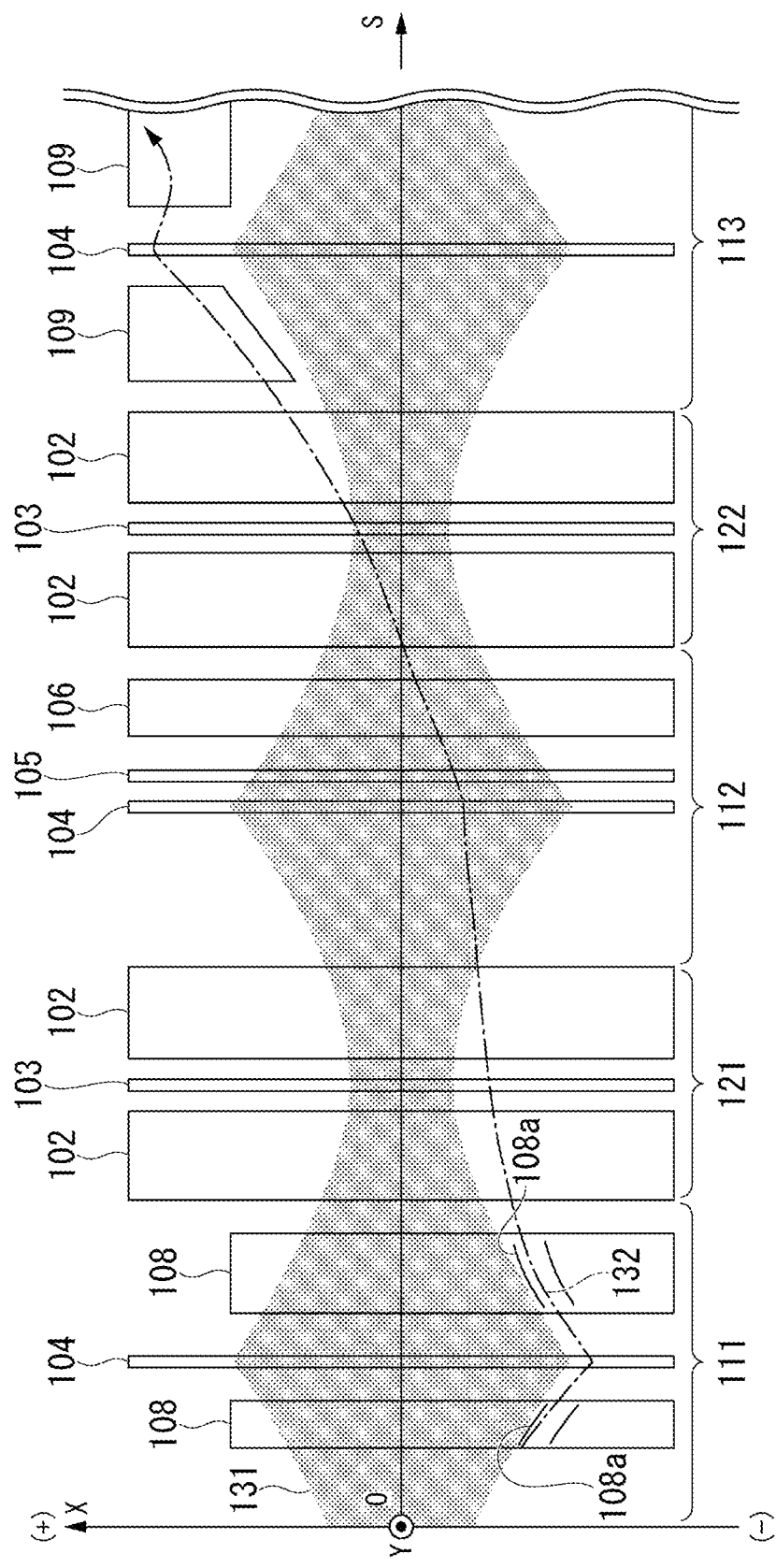
FIG. 14 is a diagram showing a relationship between a passage region of a circulating beam and a trajectory of an output beam in the synchrotron of the second embodiment.

FIG. 14 is a diagram showing a relationship between a passage region of the circulating beam 131 and a trajectory of the output beam 132 in the synchrotron (the particle accelerator) 100 of the second embodiment. In FIG. 14, an S-axis direction indicates the traveling direction of the circulating beam 131. An X axis included in a plane orthogonal to an S axis corresponds to a deflection direction of the deflection electromagnet 102, a deflection direction of the preceding output deflector 108, and a deflection direction of the succeeding output deflector 109.

In the synchrotron 100 of the second embodiment, as shown in FIG. 14, before the circulating beam 131 is caused to converge by the first converging quadrupole electromagnet 104, some of the circulating beam 131 is deflected toward the inner side of the circulating trajectory (the hatched portion in FIG. 14) of the circulating beam 131 (a lower side in FIG. 14 with respect to the circulating trajectory of the circulating beam 131) by a septum electrode 108a of the first preceding output deflector 108 to be separated as the output beam 132.

Third Embodiment

Hereinafter, a particle accelerator and a particle beam therapy apparatus according to a third embodiment of the present invention will be described.

The particle accelerator (a synchrotron 100) of the third embodiment has the same configuration as the particle accelerator (the synchrotron 100) of the above-described second embodiment except for points which will be described later. Therefore, according to the particle accelerator (the synchrotron 100) of the third embodiment, the same effects as the particle accelerator (the synchrotron 100) of the above-described second embodiment can be exhibited except for the points which will be described later.

Figure 6:
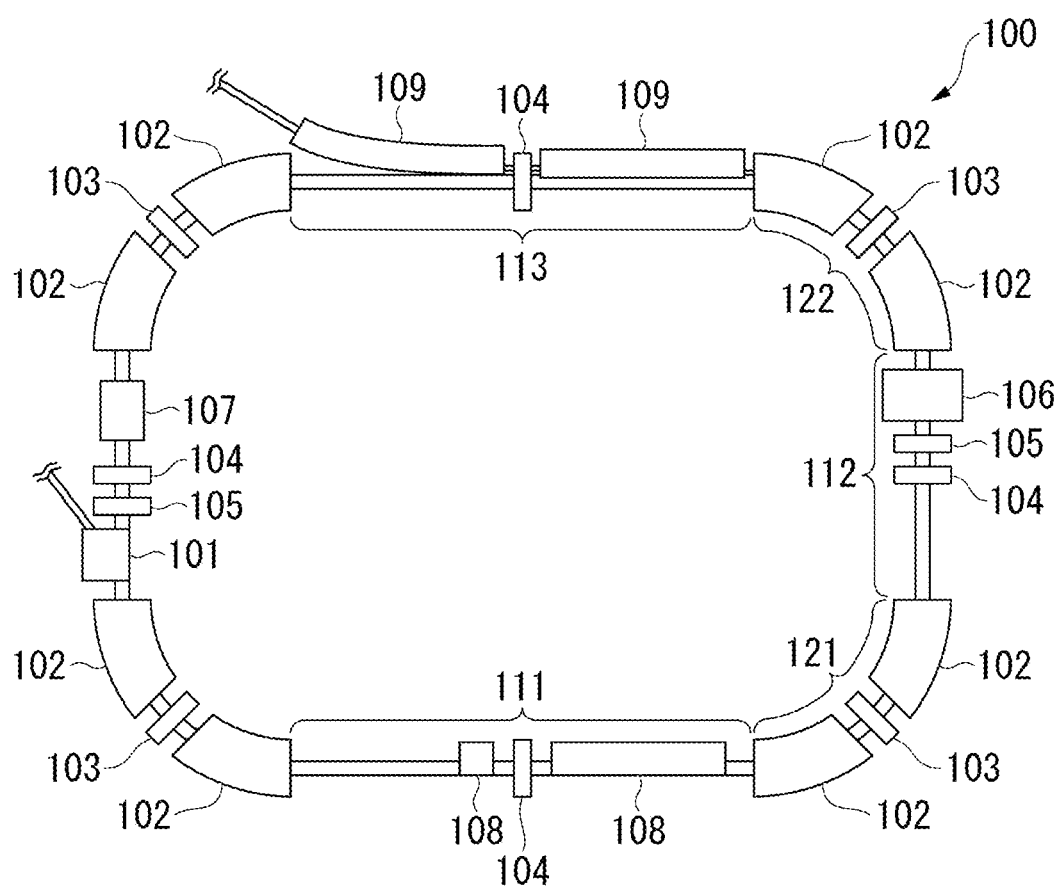
FIG. 6 is a diagram showing an example of a synchrotron (a particle accelerator) according to a third embodiment.

FIG. 6 is a diagram showing an example of the synchrotron (the particle accelerator) 100 according to the third embodiment.

In the above-described examples shown in FIGS. 1 and 5, a length of the first straight section 111, a length of the second straight section 112, and a length of the third straight section 113 are equal to each other.

In a case where it is necessary to increase the deflection angles of the preceding output deflector 108 and the succeeding output deflector 109 as compared with the examples shown in FIGS. 1 and 5, the synchrotron 100 shown in FIG. 6 is configured.

Specifically, in the example shown in FIG. 6, the length of the first straight section 111 and the length of the third straight section 113 are equal to each other, and the first straight section 111 and the third straight section 113 are longer than the second straight section 112. As in the example shown in FIG. 6, the first straight section 111 in which the preceding output deflector 108 is disposed and the third straight section 113 in which the succeeding output deflector 109 is disposed are extended without extending the second straight section 112, and thus a circumference of the synchrotron 100 can be shortened as much as possible while maintaining the minimum a device arrangement symmetry required for the synchrotron 100.

A relationship between a passage region of the circulating beam 131 and a trajectory of the output beam 132 in the synchrotron (the particle accelerator) 100 of the third embodiment is similar to the relationship shown in FIG. 14.

Fourth Embodiment

Hereinafter, a particle accelerator and a particle beam therapy apparatus according to a fourth embodiment of the present invention will be described.

The particle accelerator (a synchrotron 100) of the fourth embodiment has the same configuration as the particle accelerator (the synchrotron 100) of the above-described second embodiment except for points which will be described later. Therefore, according to the particle accelerator (the synchrotron 100) of the fourth embodiment, the same effects as the particle accelerator (the synchrotron 100) of the above-described second embodiment can be exhibited except for the points which will be described later.

Figure 7:
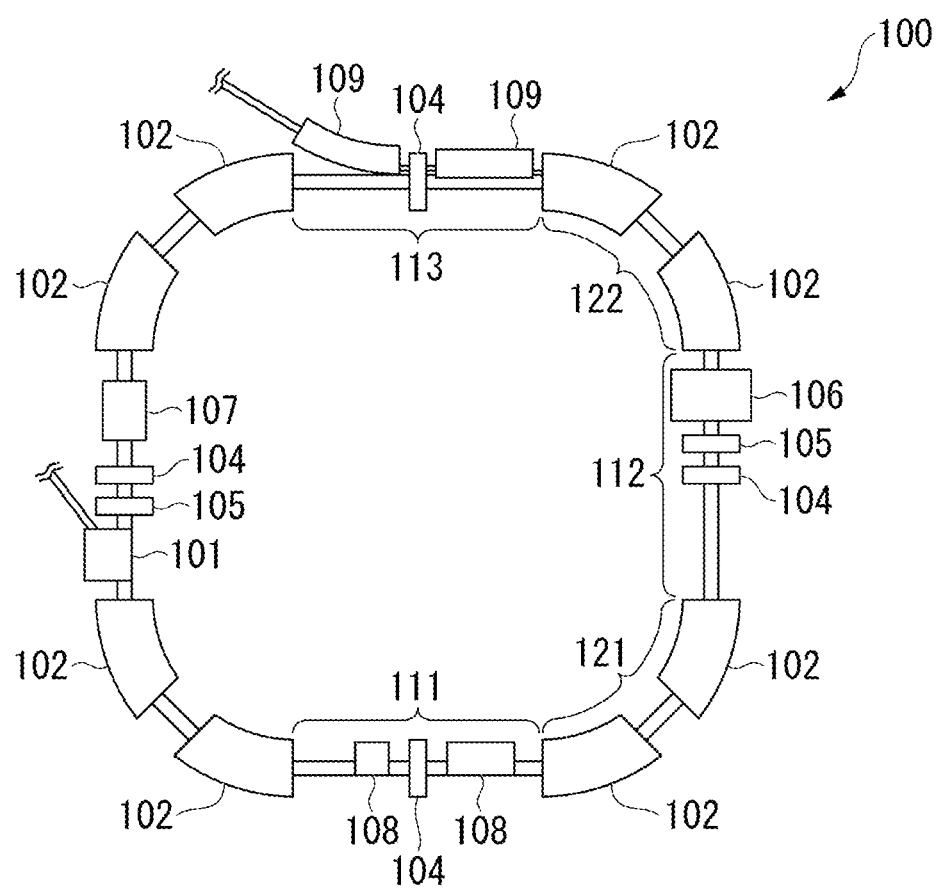
FIG. 7 is a diagram showing an example of a synchrotron (a particle accelerator) according to a fourth embodiment.

FIG. 7 is a diagram showing an example of the synchrotron (the particle accelerator) 100 according to the fourth embodiment.

In the example shown in FIG. 7, the synchrotron 100 accelerates the charged particle beam supplied from the linear accelerator of the injector 201 (see FIG. 1) while circulating the charged particle beam as a circulating beam 131 and outputs some of the circulating beam 131 as an output beam 132. The synchrotron 100 includes, for example, an injection deflector 101, eight deflection electromagnets 102, four converging quadrupole electromagnets 104, two resonance excitation multipole electromagnets 105, a high frequency acceleration cavity 106, a high frequency kicker device 107, two preceding output deflectors 108, two succeeding output deflectors 109, a control unit 140 (see FIG. 2), and a plurality of power supplies 150 (see FIG. 2).

That is, in the example shown in FIG. 7, the four diverging quadrupole electromagnets 103 (see FIG. 5) that each form the short straight section are not provided in the synchrotron 100 as compared with the example shown in FIG. 5.

In the example shown in FIG. 7, the injection deflector 101 has the same function as the injection deflector 101 shown in FIG. 1. The injection deflector 101 is connected to a first deflection electromagnet 102 disposed on a downstream side thereof in a traveling direction of the circulating beam 131.

The deflection electromagnet 102 has the same function as the deflection electromagnet 102 shown in FIG. 1. The first deflection electromagnet 102 is connected to a second deflection electromagnet 102 disposed on a downstream side thereof in the traveling direction of the circulating beam 131. The second deflection electromagnet 102 is connected to a first preceding output deflector 108 disposed on a downstream side thereof in the traveling direction of the circulating beam 131.

Each of the two preceding output deflectors 108 has the same function as the preceding output deflector 108 shown in FIG. 1. The first preceding output deflector 108 is connected to a first converging quadrupole electromagnet 104 disposed on a downstream side thereof in the traveling direction of the circulating beam 131.

The converging quadrupole electromagnet 104 has the same function as the converging quadrupole electromagnet 104 shown in FIG. 1. The first converging quadrupole electromagnet 104 is connected to a second preceding output deflector 108 disposed on a downstream side thereof in the traveling direction of the circulating beam 131.

As shown in FIG. 7, the first preceding output deflector 108, the first converging quadrupole electromagnet 104, and the second preceding output deflector 108 are provided in a first straight section 111. The first converging quadrupole electromagnet 104 is disposed substantially at a center of the first straight section 111 in the traveling direction of the circulating beam 131. The first straight section 111 does not have the deflection electromagnet 102.

In another example, three or more preceding output deflectors 108 may be provided in the first straight section 111. In still another example, either one of the first preceding output deflector 108 and the second preceding output deflector 108 may not be provided in the first straight section 111.

In the example shown in FIG. 7, the second preceding output deflector 108 is connected to a third deflection electromagnet 102 disposed on a downstream side thereof in the traveling direction of the circulating beam 131. The third deflection electromagnet 102 is connected to a fourth deflection electromagnet 102 disposed on a downstream side thereof in the traveling direction of the circulating beam 131.

As shown in FIG. 7, the third deflection electromagnet 102 and the fourth deflection electromagnet 102 are provided in a first deflection section 121.

In another example, a quadrupole magnetic field generating mechanism for a deflection section obtained by integrating the deflection electromagnet 102 and a quadrupole magnetic field coil may be provided in the first deflection section 121.

In the example shown in FIG. 7, the fourth deflection electromagnet 102 is connected to a second converging quadrupole electromagnet 104 disposed on a downstream side thereof in the traveling direction of the circulating beam 131. The second converging quadrupole electromagnet 104 is connected to a first resonance excitation multipole electromagnet 105 disposed on a downstream side thereof in the traveling direction of the circulating beam 131. The first resonance excitation multipole electromagnet 105 is connected to the high frequency acceleration cavity 106 disposed on a downstream side thereof in the traveling direction of the circulating beam 131.

As shown in FIG. 7, the second converging quadrupole electromagnet 104, the first resonance excitation multipole electromagnet 105, and the high frequency acceleration cavity 106 are provided in a second straight section 112. The second straight section 112 does not have the deflection electromagnet 102.

In the example shown in FIG. 7, the high frequency acceleration cavity 106 is connected to a fifth deflection electromagnet 102 disposed on a downstream side thereof in the traveling direction of the circulating beam 131. The fifth deflection electromagnet 102 is connected to a sixth deflection electromagnet 102 disposed on a downstream side thereof in the traveling direction of the circulating beam 131.

As shown in FIG. 7, the fifth deflection electromagnet 102 and the sixth deflection electromagnet 102 are provided in a second deflection section 122.

In another example, a quadrupole magnetic field generating mechanism for a deflection section obtained by integrating the deflection electromagnet 102 and a quadrupole magnetic field coil may be provided in the second deflection section 122.

In the example shown in FIG. 7, the sixth deflection electromagnet 102 is connected to a first succeeding output deflector 109 disposed on a downstream side thereof in the traveling direction of the circulating beam 131.

Each of the two succeeding output deflectors 109 has the same function as the succeeding output deflector 109 shown in FIG. 1. The first succeeding output deflector 109 is connected to a third converging quadrupole electromagnet 104 disposed on a downstream side thereof in the traveling direction of the circulating beam 131.

The third converging quadrupole electromagnet 104 is connected to a second succeeding output deflector 109 disposed on a downstream side thereof in the traveling direction of the circulating beam 131.

As shown in FIG. 7, the first succeeding output deflector 109, the third converging quadrupole electromagnet 104, and the second succeeding output deflector 109 are provided in a third straight section 113. The third converging quadrupole electromagnet 104 is disposed substantially at a center of the third straight section 113 in the traveling direction of the circulating beam 131. The third straight section 113 does not have the deflection electromagnet 102.

In another example, three or more succeeding output deflectors 109 may be provided in the third straight section 113. In still another example, either one of the first succeeding output deflector 109 and the second succeeding output deflector 109 may not be provided in the third straight section 113.

In the example shown in FIG. 7, the third converging quadrupole electromagnet 104 is connected to a seventh deflection electromagnet 102 disposed on a downstream side thereof in the traveling direction of the circulating beam 131. The seventh deflection electromagnet 102 is connected to an eighth deflection electromagnet 102 disposed on a downstream side thereof in the traveling direction of the circulating beam 131.

The eighth deflection electromagnet 102 is connected to the high frequency kicker device 107 disposed on a downstream side thereof in the traveling direction of the circulating beam 131. The high frequency kicker device 107 is connected to a fourth converging quadrupole electromagnet 104 disposed on a downstream side thereof in the traveling direction of the circulating beam 131. The fourth converging quadrupole electromagnet 104 is connected to a second resonance excitation multipole electromagnet 105 disposed on a downstream side thereof in the traveling direction of the circulating beam 131. The second resonance excitation multipole electromagnet 105 is connected to the injection deflector 101 disposed on a downstream side thereof in the traveling direction of the circulating beam 131.

In the example shown in FIG. 7, the control unit 140 adjusts the quadrupole electromagnet 104 of the first straight section 111, the quadrupole electromagnet 104 of the second straight section 112, and the quadrupole electromagnet 104 of the third straight section 113 such that a phase advance of a betatron oscillation of the output beam 132 is 270±45 degrees in a section from the preceding output deflector 108 to the succeeding output deflector 109.

Specifically, the control unit 140 adjusts the quadrupole electromagnet 104 of the first straight section 111, the quadrupole electromagnet 104 of the second straight section 112, and the quadrupole electromagnet 104 of the third straight section 113 such that a phase advance of a betatron oscillation of the output beam 132 is 270±45 degrees in a section from the preceding output deflector 108 to the succeeding output deflector 109.

In parallel with this, the control unit 140 adjusts electric field intensity of the preceding output deflector 108 such that the output beam 132 passes through the vicinity of a passage region of the circulating beam 131 in the first deflection section 121, the output beam 132 passes through a passage region of the circulating beam 131 in the second deflection section 122 or passes through the vicinity of the passage region of the circulating beam 131 in the second deflection section 122, and the output beam 132 passes through a position spaced apart from a passage region of the circulating beam 131 in third straight section 113.

A relationship between a passage region of the circulating beam 131 and a trajectory of the output beam 132 in the synchrotron (the particle accelerator) 100 of the fourth embodiment is similar to the relationship shown in FIG. 14.

Fifth Embodiment

Hereinafter, a particle accelerator and a particle beam therapy apparatus according to a fifth embodiment of the present invention will be described.

The particle accelerator (a synchrotron 100) of the fifth embodiment has the same configuration as the particle accelerator (the synchrotron 100) of the above-described fourth embodiment except for points which will be described later. Therefore, according to the particle accelerator (the synchrotron 100) of the fifth embodiment, the same effects as the particle accelerator (the synchrotron 100) of the above-described fourth embodiment can be exhibited except for the points which will be described later.

Figure 8:
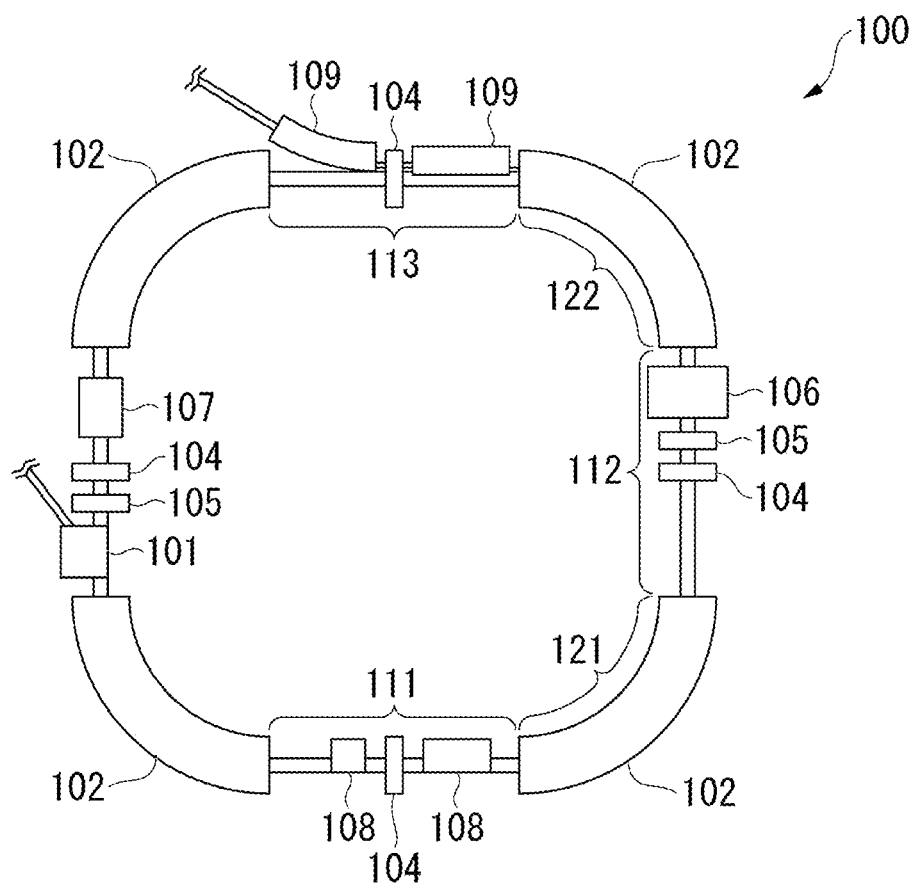
FIG. 8 is a diagram showing an example of a synchrotron (a particle accelerator) according to a fifth embodiment.
Figure 9:
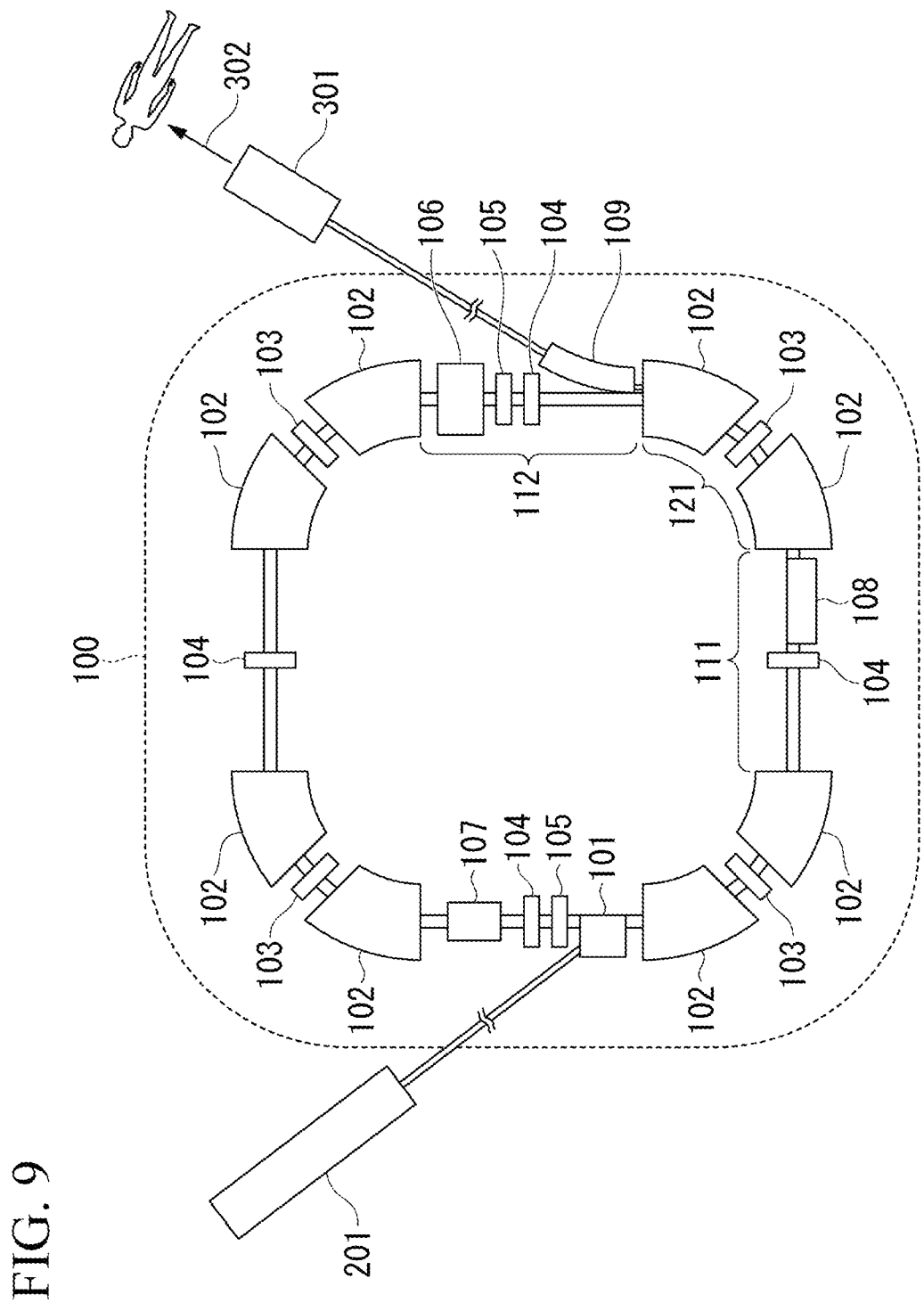
FIG. 9 is a diagram showing a particle accelerator of the related art and a particle beam therapy apparatus to which the particle accelerator is applied.

FIG. 8 is a diagram showing an example of the synchrotron (the particle accelerator) 100 according to the fifth embodiment.

In the example shown in FIG. 8, the synchrotron 100 accelerates the charged particle beam supplied from the linear accelerator of the injector 201 (see FIG. 1) while circulating the charged particle beam as a circulating beam 131 and outputs some of the circulating beam 131 as the output beam 132. The synchrotron 100 includes, for example, an injection deflector 101, four deflection electromagnets 102, four converging quadrupole electromagnets 104, two resonance excitation multipole electromagnets 105, a high frequency acceleration cavity 106, a high frequency kicker device 107, two preceding output deflectors 108, two succeeding output deflectors 109, a control unit 140 (see FIG. 2), and a plurality of power supplies 150 (see FIG. 2).

That is, in the example shown in FIG. 8, the first deflection electromagnet 102 and the second deflection electromagnet 102 in the example shown in FIG. 7 are merged with each other to form a first deflection electromagnet 102. Further, in the example shown in FIG. 8, the third deflection electromagnet 102 and the fourth deflection electromagnet 102 in the example shown in FIG. 7 are merged with each other to form a second deflection electromagnet 102, the fifth deflection electromagnet 102 and the sixth deflection electromagnet 102 in the example shown in FIG. 7 are merged with each other to form a third deflection electromagnet 102, and the seventh deflection electromagnet 102 and the eighth deflection electromagnet 102 in the example shown in FIG. 7 are merged with each other to form a fourth deflection electromagnet 102.

In the example shown in FIG. 8, the injection deflector 101 has the same function as the injection deflector 101 shown in FIG. 1. The injection deflector 101 is connected to the first deflection electromagnet 102 disposed on a downstream side thereof in a traveling direction of the circulating beam 131.

The deflection electromagnet 102 has the same function as the deflection electromagnet 102 shown in FIG. 1. The first deflection electromagnet 102 is connected to a first preceding output deflector 108 disposed on a downstream side thereof in the traveling direction of the circulating beam 131.

Each of the two preceding output deflectors 108 has the same function as the preceding output deflector 108 shown in FIG. 1. The first preceding output deflector 108 is connected to a first converging quadrupole electromagnet 104 disposed on a downstream side thereof in the traveling direction of the circulating beam 131.

The converging quadrupole electromagnet 104 has the same function as the converging quadrupole electromagnet 104 shown in FIG. 1. The first converging quadrupole electromagnet 104 is connected to a second preceding output deflector 108 disposed on a downstream side thereof in the traveling direction of the circulating beam 131.

As shown in FIG. 8, the first preceding output deflector 108, the first converging quadrupole electromagnet 104, and the second preceding output deflector 108 are provided in a first straight section 111. The first converging quadrupole electromagnet 104 is disposed substantially at a center of the first straight section 111 in the traveling direction of the circulating beam 131. The first straight section 111 does not have the deflection electromagnet 102.

In another example, three or more preceding output deflectors 108 may be provided in the first straight section 111. In still another example, either one of the first preceding output deflector 108 and the second preceding output deflector 108 may not be provided in the first straight section 111.

In the example shown in FIG. 8, the second preceding output deflector 108 is connected to the second deflection electromagnet 102 disposed on a downstream side thereof in the traveling direction of the circulating beam 131. The second deflection electromagnet 102 is connected to a second converging quadrupole electromagnet 104 disposed on a downstream side thereof in the traveling direction of the circulating beam 131.

As shown in FIG. 8, the second deflection electromagnet 102 is provided in a first deflection section 121.

In another example, a quadrupole magnetic field generating mechanism for a deflection section obtained by integrating the deflection electromagnet 102 and a quadrupole magnetic field coil may be provided in the first deflection section 121.

In the example shown in FIG. 8, the second converging quadrupole electromagnet 104 is connected to a first resonance excitation multipole electromagnet 105 disposed on a downstream side thereof in the traveling direction of the circulating beam 131. The first resonance excitation multipole electromagnet 105 is connected to the high frequency acceleration cavity 106 disposed on a downstream side thereof in the traveling direction of the circulating beam 131.

As shown in FIG. 8, the second converging quadrupole electromagnet 104, the first resonance excitation multipole electromagnet 105, and the high frequency acceleration cavity 106 are provided in a second straight section 112. The second straight section 112 does not have the deflection electromagnet 102.

In the example shown in FIG. 8, the high frequency acceleration cavity 106 is connected to the third deflection electromagnet 102 disposed on a downstream side thereof in the traveling direction of the circulating beam 131. The third deflection electromagnet 102 is connected to a first succeeding output deflector 109 disposed on a downstream side thereof in the traveling direction of the circulating beam 131.

As shown in FIG. 8, the third deflection electromagnet 102 is provided in a second deflection section 122.

In another example, a quadrupole magnetic field generating mechanism for a deflection section obtained by integrating the deflection electromagnet 102 and a quadrupole magnetic field coil may be provided in the second deflection section 122.

In the example shown in FIG. 8, each of the two succeeding output deflectors 109 has the same function as the succeeding output deflector 109 shown in FIG. 1. The first succeeding output deflector 109 is connected to a third converging quadrupole electromagnet 104 disposed on a downstream side thereof in the traveling direction of the circulating beam 131.

The third converging quadrupole electromagnet 104 is connected to a second succeeding output deflector 109 disposed on a downstream side thereof in the traveling direction of the circulating beam 131.

As shown in FIG. 8, the first succeeding output deflector 109, the third converging quadrupole electromagnet 104, and the second succeeding output deflector 109 are provided in a third straight section 113. The third converging quadrupole electromagnet 104 is disposed substantially at a center of the third straight section 113 in the traveling direction of the circulating beam 131. The third straight section 113 does not have the deflection electromagnet 102.

In another example, three or more succeeding output deflectors 109 may be provided in the third straight section 113. In still another example, either one of the first succeeding output deflector 109 and the second succeeding output deflector 109 may not be provided in the third straight section 113.

In the example shown in FIG. 8, the third converging quadrupole electromagnet 104 is connected to the fourth deflection electromagnet 102 disposed on a downstream side thereof in the traveling direction of the circulating beam 131. The fourth deflection electromagnet 102 is connected to the high frequency kicker device 107 disposed on a downstream side thereof in the traveling direction of the circulating beam 131.

The high frequency kicker device 107 is connected to a fourth converging quadrupole electromagnet 104 disposed on a downstream side thereof in the traveling direction of the circulating beam 131. The fourth converging quadrupole electromagnet 104 is connected to a second resonance excitation multipole electromagnet 105 disposed on a downstream side thereof in the traveling direction of the circulating beam 131. The second resonance excitation multipole electromagnet 105 is connected to the injection deflector 101 disposed on a downstream side thereof in the traveling direction of the circulating beam 131.

A relationship between a passage region of the circulating beam 131 and a trajectory of the output beam 132 in the synchrotron (the particle accelerator) 100 of the fifth embodiment is similar to the relationship shown in FIG. 14.

Sixth Embodiment

Hereinafter, a particle accelerator and a particle beam therapy apparatus according to a sixth embodiment of the present invention will be described.

The particle accelerator (a synchrotron 100) of the sixth embodiment has the same configuration as the particle accelerator (the synchrotron 100) of the above-described fourth embodiment except for points which will be described later. Therefore, according to the particle accelerator (the synchrotron 100) of the sixth embodiment, the same effects as the particle accelerator (the synchrotron 100) of the above-described fourth embodiment can be exhibited except for the points which will be described later.

Figure 12:
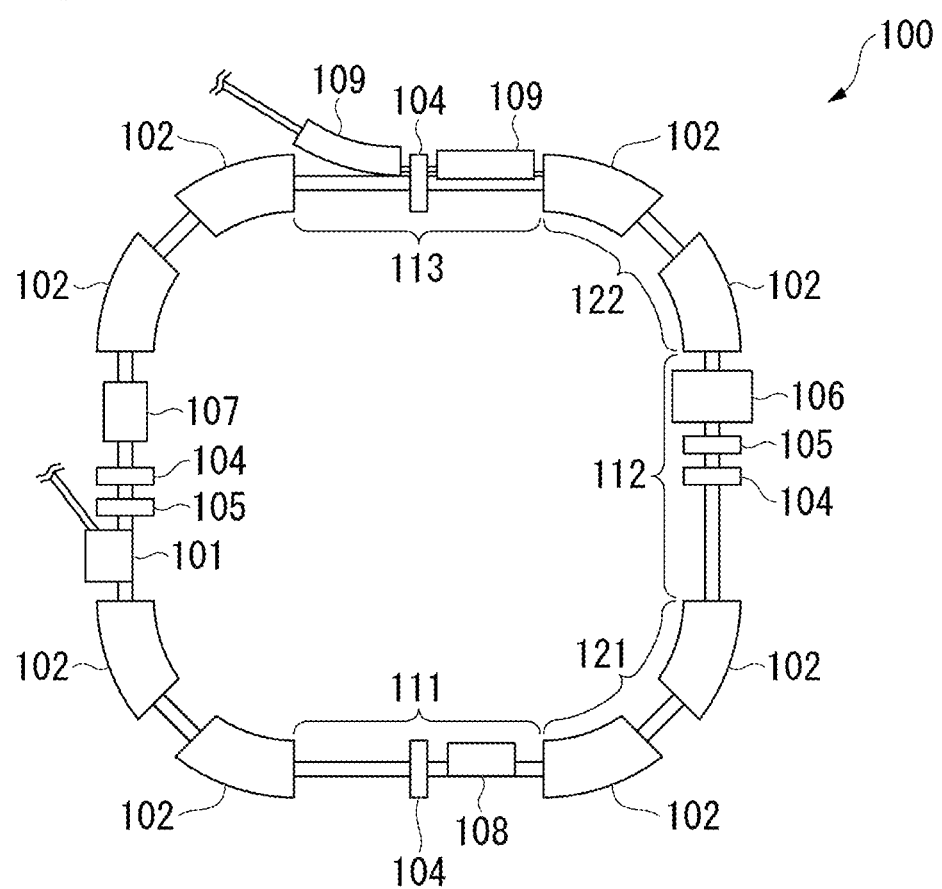
FIG. 12 is a diagram showing an example of a synchrotron (a particle accelerator) according to a sixth embodiment.

FIG. 12 is a diagram showing an example of the synchrotron (the particle accelerator) 100 according to the sixth embodiment.

In the example shown in FIG. 12, the synchrotron 100 accelerates the charged particle beam supplied from the linear accelerator of the injector 201 (see FIG. 1) while circulating the charged particle beam as a circulating beam 131 and outputs some of the circulating beam 131 as an output beam 132. The synchrotron 100 includes, for example, an injection deflector 101, eight deflection electromagnets 102, four converging quadrupole electromagnets 104, two resonance excitation multipole electromagnets 105, a high frequency acceleration cavity 106, a high frequency kicker device 107, one preceding output deflectors 108, two succeeding output deflectors 109, a control unit 140 (see FIG. 2), and a plurality of power supplies 150 (see FIG. 2).

That is, in the example shown in FIG. 7, the synchrotron 100 includes two preceding output deflectors 108, whereas in the example shown in FIG. 12, the synchrotron 100 includes one preceding output deflector 108.

In the example shown in FIG. 12, the injection deflector 101 has the same function as the injection deflector 101 shown in FIG. 1. The injection deflector 101 is connected to the first deflection electromagnet 102 disposed on a downstream side thereof in a traveling direction of the circulating beam 131.

The deflection electromagnet 102 has the same function as the deflection electromagnet 102 shown in FIG. 1. The first deflection electromagnet 102 is connected to a second deflection electromagnet 102 disposed on a downstream side thereof in the traveling direction of the circulating beam 131. The second deflection electromagnet 102 is connected to a first converging quadrupole electromagnet 104 disposed on a downstream side thereof in the traveling direction of the circulating beam 131.

The converging quadrupole electromagnet 104 has the same function as the converging quadrupole electromagnet 104 shown in FIG. 1. The first converging quadrupole electromagnet 104 is connected to the preceding output deflector 108 disposed on a downstream side thereof in the traveling direction of the circulating beam 131.

The preceding output deflectors 108 has the same function as the preceding output deflector 108 shown in FIG. 1. The preceding output deflector 108 is connected to a third deflection electromagnet 102 disposed on a downstream side thereof in a traveling direction of the circulating beam 131.

As shown in FIG. 12, the first converging quadrupole electromagnet 104 and the preceding output deflector 108 are provided in a first straight section 111. The first converging quadrupole electromagnet 104 is disposed substantially at a center of the first straight section 111 in the traveling direction of the circulating beam 131. The first straight section 111 does not have the deflection electromagnet 102.

A relationship between a passage region of the circulating beam 131 and a trajectory of the output beam 132 in the synchrotron (the particle accelerator) 100 of the sixth embodiment is similar to the relationship shown in FIG. 3.

Seventh Embodiment

Hereinafter, a particle accelerator and a particle beam therapy apparatus according to a seventh embodiment of the present invention will be described.

The particle accelerator (a synchrotron 100) of the seventh embodiment has the same configuration as the particle accelerator (the synchrotron 100) of the above-described fifth embodiment except for points which will be described later. Therefore, according to the particle accelerator (the synchrotron 100) of the seventh embodiment, the same effects as the particle accelerator (the synchrotron 100) of the above-described fifth embodiment can be exhibited except for the points which will be described later.

Figure 13:
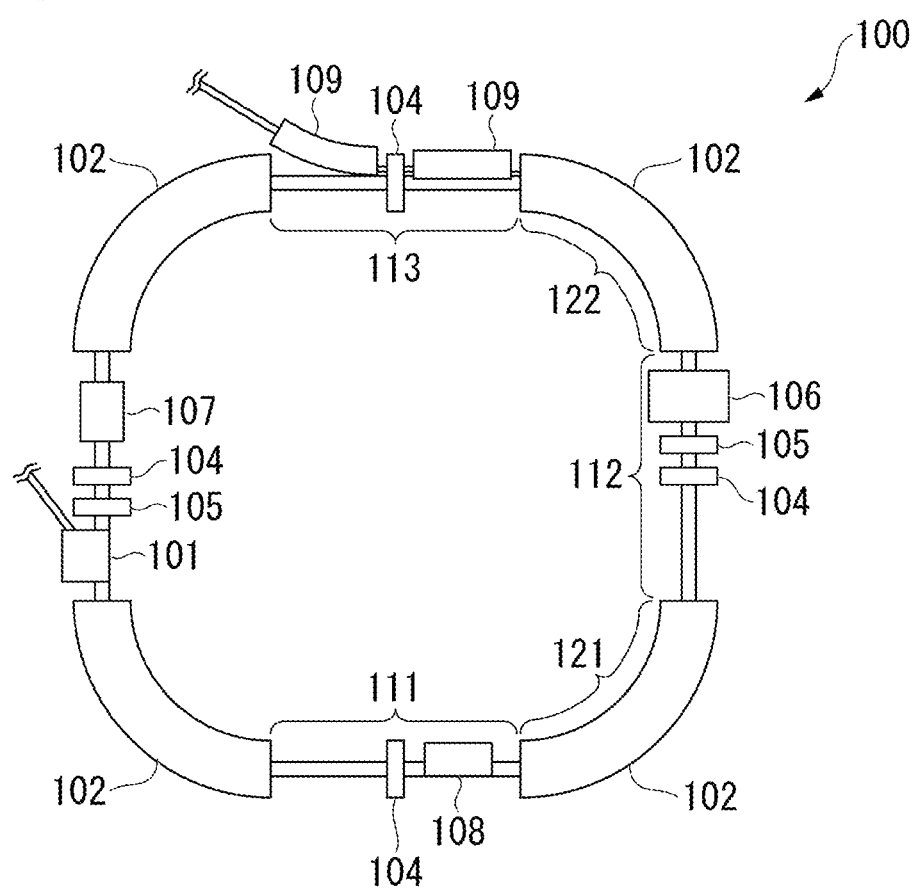
FIG. 13 is a diagram showing an example of a synchrotron (a particle accelerator) according to a seventh embodiment.

FIG. 13 is a diagram showing an example of the synchrotron (the particle accelerator) 100 according to the seventh embodiment.

In the example shown in FIG. 13, the synchrotron 100 accelerates the charged particle beam supplied from the linear accelerator of the injector 201 (see FIG. 1) while circulating the charged particle beam as a circulating beam 131 and outputs some of the circulating beam 131 as an output beam 132. The synchrotron 100 includes, for example, an injection deflector 101, four deflection electromagnets 102, four converging quadrupole electromagnets 104, two resonance excitation multipole electromagnets 105, a high frequency acceleration cavity 106, a high frequency kicker device 107, one preceding output deflectors 108, two succeeding output deflectors 109, a control unit 140 (see FIG. 2), and a plurality of power supplies 150 (see FIG. 2).

That is, in the example shown in FIG. 8, the synchrotron 100 includes two preceding output deflectors 108, whereas in the example shown in FIG. 13, the synchrotron 100 includes one preceding output deflector 108.

In the example shown in FIG. 13, the injection deflector 101 has the same function as the injection deflector 101 shown in FIG. 1. The injection deflector 101 is connected to a first deflection electromagnet 102 disposed on a downstream side thereof in a traveling direction of the circulating beam 131.

The deflection electromagnet 102 has the same function as the deflection electromagnet 102 shown in FIG. 1. The first deflection electromagnet 102 is connected to a first converging quadrupole electromagnet 104 disposed on a downstream side thereof in the traveling direction of the circulating beam 131.

The converging quadrupole electromagnet 104 has the same function as the converging quadrupole electromagnet 104 shown in FIG. 1. The first converging quadrupole electromagnet 104 is connected to the preceding output deflector 108 disposed on a downstream side thereof in the traveling direction of the circulating beam 131.

The preceding output deflectors 108 has the same function as the preceding output deflector 108 shown in FIG. 1. The preceding output deflector 108 is connected to a second deflection electromagnet 102 disposed on a downstream side thereof in a traveling direction of the circulating beam 131.

As shown in FIG. 13, the first converging quadrupole electromagnet 104 and the preceding output deflector 108 are provided in a first straight section 111. The first converging quadrupole electromagnet 104 is disposed substantially at a center of the first straight section 111 in the traveling direction of the circulating beam 131. The first straight section 111 does not have the deflection electromagnet 102.

A relationship between a passage region of the circulating beam 131 and a trajectory of the output beam 132 in the synchrotron (the particle accelerator) 100 of the seventh embodiment is similar to the relationship shown in FIG. 3.

Although the embodiments for carrying out the present invention have been described above using the embodiments, the present invention is not limited to these embodiments, and various modifications and substitutions can be added without departing from the gist of the present invention. The configurations described in each embodiment and each example described above may be combined with each other.

REFERENCE SIGNS LIST

100 Synchrotron (particle accelerator)
101 Injection deflector
102 Deflection electromagnet
103 (Diverging) quadrupole electromagnet
104 (Converging) quadrupole electromagnet
105 Resonance excitation multipole electromagnet
106 High frequency acceleration cavity
107 High frequency kicker device
108 Preceding output deflector
108*a* Septum electrode
109 Succeeding output deflector
111 (First) straight section
112 (Second) straight section
113 (Third) straight section
121 (First) deflection section
122 (Second) deflection section
131 Circulating beam
132 Output beam
140 Control unit
150 Power supply
201 Injector
301 Irradiation device
302 Irradiation beam
302*a* Two-dimensional cross-sectional distribution
302*b* Horizontal projection profile
302*c* Vertical projection profile
302*a*' Two-dimensional cross-sectional distribution
302*b*' Horizontal projection profile
302*c*' Vertical projection profile

The invention claimed is:

1. A particle accelerator that accelerates a charged particle beam while circulating the charged particle beam as a circulating beam and outputs some of the circulating beam as an output beam, the particle accelerator comprising:
a plurality of deflection sections each having a deflection electromagnet;
a plurality of straight sections each not having the deflection electromagnet; and
a control unit,
wherein the plurality of straight sections include
a first straight section having a preceding output deflector,
a second straight section that is disposed on a downstream side of the first straight section in a traveling direction of the circulating beam and has a quadrupole electromagnet, and
a third straight section that is disposed on a downstream side of the second straight section in the traveling direction of the circulating beam and has a succeeding output deflector,
wherein the plurality of deflection sections include
a first deflection section connecting the first straight section and the second straight section to each other, and
a second deflection section connecting the second straight section and the third straight section to each other,
wherein the preceding output deflector deflects some of the circulating beam toward one of an inner side and an outer side of a circulating trajectory of the circulating beam to separate the some of the circulating beam as an output beam,
wherein the succeeding output deflector deflects the output beam separated from the circulating beam by the preceding output deflector toward the other of the inner side and the outer side of the circulating trajectory of the circulating beam, and
wherein the control unit controls at least the quadrupole electromagnet such that a phase advance of a betatron oscillation of the output beam is 270±45 degrees in a section from the preceding output deflector to the succeeding output deflector.

2. The particle accelerator according to claim 1,
wherein the control unit controls at least the quadrupole electromagnet such that a phase advance of a betatron oscillation of the output beam is 270±45 degrees in a section from the preceding output deflector to the succeeding output deflector, and
wherein the control unit controls the preceding output deflector such that the output beam passes through the vicinity of a passage region of the circulating beam in the first deflection section, the output beam passes through a passage region of the circulating beam in the second deflection section or passes through the vicinity of the passage region of the circulating beam in the second deflection section, and the output beam passes through a position spaced apart from a passage region of the circulating beam in third straight section.

3. The particle accelerator according to claim 1, wherein the first straight section and the third straight section are disposed at positions facing each other on the circulating trajectory of the circulating beam.

4. The particle accelerator according to claim 3, wherein the first straight section and the third straight section extend parallel to each other.

5. The particle accelerator according to claim 1,
wherein each of the plurality of deflection sections has the deflection electromagnet and a deflection section quadrupole electromagnet or has a quadrupole magnetic field generating mechanism for a deflection section obtained by integrating the deflection electromagnet and a quadrupole magnetic field coil,
wherein each of the plurality of straight sections has the quadrupole electromagnet, and wherein the control unit adjusts an amount of excitation of the deflection section quadrupole electromagnet of each of the plurality of deflection sections or an amount of excitation of the quadrupole magnetic field generating mechanism for a deflection section and an amount of excitation of the quadrupole electromagnet of each of the plurality of straight sections such that a phase advance of a betatron oscillation of the output beam is 270±45 degrees in a section from the preceding output deflector to the succeeding output deflector.

6. The particle accelerator according to claim 5,
wherein the control unit adjusts an amount of excitation of the deflection section quadrupole electromagnet of each of the plurality of deflection sections or an amount of excitation of the quadrupole magnetic field generating mechanism for a deflection section and an amount of excitation of the quadrupole electromagnet of each of the plurality of straight sections such that a phase advance of a betatron oscillation of the output beam is 270±45 degrees in a section from the preceding output deflector to the succeeding output deflector, and
wherein the control unit adjusts electric field intensity of the preceding output deflector such that the output beam passes through the vicinity of a passage region of the circulating beam in the first deflection section, the output beam passes through a passage region of the circulating beam in the second deflection section or passes through the vicinity of the passage region of the circulating beam in the second deflection section, and the output beam passes through a position spaced apart from a passage region of the circulating beam in third straight section.

7. The particle accelerator according to claim 1,
wherein each of the plurality of straight sections has the quadrupole electromagnet, and
wherein the control unit adjusts the quadrupole electromagnet of each of the plurality of straight sections such that a phase advance of a betatron oscillation of the output beam is 270±45 degrees in a section from the preceding output deflector to the succeeding output deflector.

8. The particle accelerator according to claim 7,
wherein the control unit adjusts the quadrupole electromagnet of each of the plurality of straight sections such that a phase advance of a betatron oscillation of the output beam is 270±45 degrees in a section from the preceding output deflector to the succeeding output deflector, and
wherein the control unit adjusts electric field intensity of the preceding output deflector such that the output beam passes through the vicinity of a passage region of the circulating beam in the first deflection section, the output beam passes through a passage region of the circulating beam in the second deflection section or passes through the vicinity of the passage region of the circulating beam in the second deflection section, and the output beam passes through a position spaced apart from a passage region of the circulating beam in third straight section.

9. The particle accelerator according to claim 1, wherein a deflection angle of the charged particle beam caused by the first deflection section is 60 degrees or more.

10. The particle accelerator according to claim 1, wherein a total deflection angle of the charged particle beam caused by the first deflection section and the second deflection section is 180 degrees.

11. The particle accelerator according to claim 1,
wherein each of the first straight section and the third straight section has the quadrupole electromagnet,
wherein the preceding output deflector is disposed on a downstream side of the quadrupole electromagnet of the first straight section in the traveling direction of the circulating beam, and
wherein the succeeding output deflector is disposed on a downstream side of the quadrupole electromagnet of the third straight section in the traveling direction of the circulating beam.

12. The particle accelerator according to claim 1,
wherein the quadrupole electromagnet of the first straight section is disposed substantially at a center of the first straight section in the traveling direction of the circulating beam, and
wherein the quadrupole electromagnet of the third straight section is disposed substantially at a center of the third straight section in the traveling direction of the circulating beam.

13. A particle beam therapy apparatus comprising:
the particle accelerator according to claim 1; and
an irradiation device that transports the charged particle beam extracted as the output beam from the particle accelerator and irradiates an irradiation target.

* * * * *